(12) United States Patent
Mary et al.

(10) Patent No.: US 8,785,604 B2
(45) Date of Patent: Jul. 22, 2014

(54) ANTI-CD28 HUMANIZED ANTIBODIES

(75) Inventors: Caroline Mary, Sainte Pazanne (FR);
Nicolas Poirier, Treillières (FR);
Bernard Vanhove, Reze (FR)

(73) Assignees: Effimune, Nantes (FR); Insitut National de la Sante et de la Recherche Medicale (INSERM), Paris (FR)

( * ) Notice: Subject to any disclaimer, the term of this patent is extended or adjusted under 35 U.S.C. 154(b) by 0 days.

(21) Appl. No.: 13/577,103

(22) PCT Filed: Feb. 16, 2011

(86) PCT No.: PCT/IB2011/050646
§ 371 (c)(1),
(2), (4) Date: Sep. 27, 2012

(87) PCT Pub. No.: WO2011/101791
PCT Pub. Date: Aug. 25, 2011

(65) Prior Publication Data
US 2013/0078236 A1    Mar. 28, 2013

(30) Foreign Application Priority Data

Feb. 18, 2010  (EP) .................................... 10290080
Jul. 13, 2010  (EP) .................................... 10290389

(51) Int. Cl.
*C07K 16/28* (2006.01)
*A61K 39/395* (2006.01)

(52) U.S. Cl.
USPC .............. 530/388.22; 530/388.75; 424/144.1; 424/154.1

(58) Field of Classification Search
None
See application file for complete search history.

(56) References Cited

U.S. PATENT DOCUMENTS

| 2005/0142642 A1 | 6/2005 | Sun et al. |
| 2008/0025994 A1 | 1/2008 | Steward et al. |
| 2008/0038273 A1 * | 2/2008 | Soulillou et al. ........... 424/144.1 |

FOREIGN PATENT DOCUMENTS

| WO | 02/051871 | 7/2002 |
| WO | 2004/058820 | 7/2004 |
| WO | 2010/009391 | 1/2010 |
| WO | 2010/070047 | 6/2010 |
| WO | 2010/082136 | 7/2010 |

OTHER PUBLICATIONS

Kashmin, SRD Grafting—A New Approach to Antibody Humanization, Methods, 36, pp. 25-34, 2005.
Tan, Humanization of an Anti-CD28 Antibody Using Germline Human Antibody Sequences, Blood, 96, p. 31A, 2000.
Poirier, Inducing CTLA-4-Dependent Immune Regulation by Selective CD28 Blockade Promotes Regulatory T Cells in Organ Transplantation, Science Translational Medicine, 2, pp. 1-11, 2010.
Saldanha, Molecular Engineering I: Humanization, Handbook of Therapeutic Antibodies, pp. 119-144, 2007.
Vanhove, Selective Blockade of CD28 and Not CTLA-4 with a Single-Chain Fv-alpha1-Antitrypsin Fusion Antibody, Blood. 102, pp. 564-570, 2003.
Nunes, CD28 mAbs With Distinct Binding Properties Differ in their Ability to Induce T Cell Activation: Analysis of Early and Late Activation Events, International Immunology, 5, pp. 311-315, 1993.

* cited by examiner

*Primary Examiner* — Ilia Ouspenski
(74) *Attorney, Agent, or Firm* — Morgan, Lewis & Bockius LLP

(57) ABSTRACT

The invention relates to humanized antibodies directed against the human lymphocyte receptor CD28. When used in a monovalent form these antibodies are antagonists, i.e. capable of blocking of the CD28/B7 interaction, without activating CD28. These antibodies can be used in particular as therapeutic agents for blocking T cell activation through the CD28 receptor.

14 Claims, 11 Drawing Sheets

Figure 8:
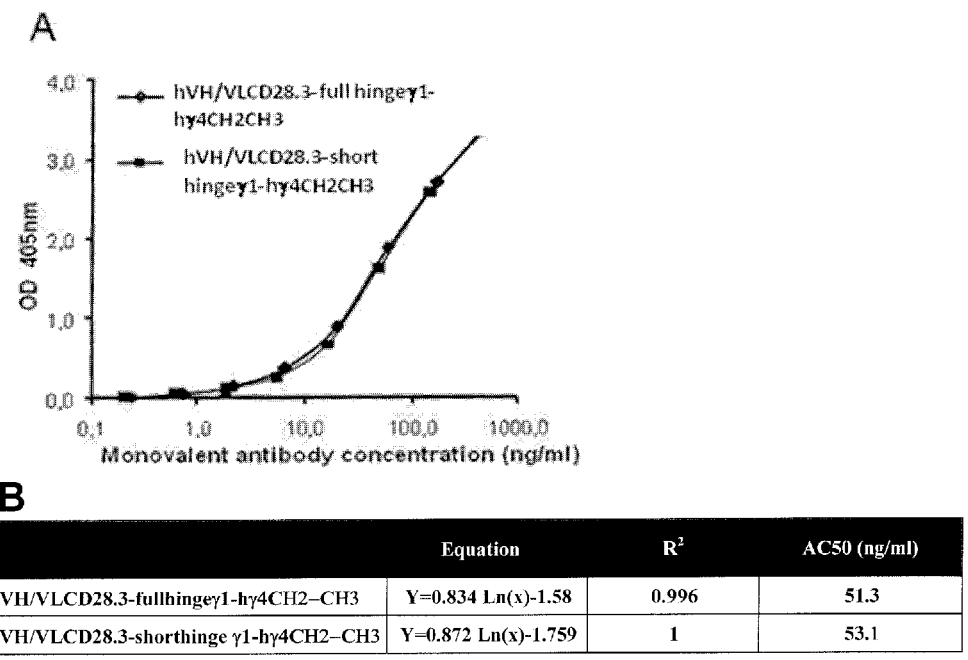

```
         ATG GAA TGG TGC TGG GTC TTT CTC TTC CTC CTG TCA GTA ACT GCA GGT GTC CAC TCC AAG GTC CAA CTG CAG CAG TCT GGA GCT    8
          M   E   W   C   W   V   F   L   F   L   L   S   V   T   A   G   V   H   S   K   V   Q   L   Q   Q   S   G   A
                                                                                                       1
  9           V12K        R19K L20V                                                                                          37
GAG CTG AAG AAA CCC GGG GCG TCG GTG AAA GTC TCC TGC AAG GCG TCT GGT TAC ACC TTC ACT GAA TAT ATT ATA CAC TGG ATA AAG
 E   L   K   K   P   G   A   S   V   K   V   S   C   K   A   S   G   Y   T   F   T   E   Y   I   I   H   W   I   K

38                                                                       K62Q                                               66
CTG AGG TCT GGA CAG GGT CTT GAG TGG ATT GGG TGG TTT TAC CCT GGA AGT AAT GAT ATA CAG TAC AAT GCG CAA TTC AAG CCC AAG
 L   R   S   G   Q   G   L   E   W   I   G   W   F   Y   P   G   S   N   D   I   Q   Y   N   A   Q   F   K   P   K

67                                                        S84P                                                              95
GCC ACA TTG ACT GCG GAC AAA TCC TCC AGC ACC GTC TAT ATG GAA CTT ACT GGA TTG ACA CCC GAG GAC TCT GCG GTC TAT TTT TGT
 A   T   L   T   A   D   K   S   S   S   T   V   Y   M   E   L   T   G   L   T   P   E   D   S   A   V   Y   F   C 96                                                                                                                         124
GCA AGA CCC GAC GAT TTC TCT GGT TAC GAC GCC CTT CCT TAC TGG GGC CAA GGG ACT CTG GTC ACT GTC TCT GCA GCT AGC ACC AAG
 A   R   P   D   D   F   S   G   Y   D   A   L   P   Y   W   G   Q   G   T   L   V   T   V   S   A   A   S   T   K 125                                                                                                                         153
GGC CCA TCG GTC TTC CCC CTG GCA CCC TCC TCC AAG AGC ACC TCT GGG GGC ACA GCG GCC CTG GGC TGC CTG GTC AAG GAC TAC TTC
 G   P   S   V   F   P   L   A   P   S   S   K   S   T   S   G   G   T   A   A   L   G   C   L   V   K   D   Y   F 154                                                                                                                         182
CCC GAA CCG GTG ACG GTG TCG TGG AAC TCA GGC GCC CTG ACC AGC GGC GTG CAC ACC TTC CCG GCT GTC CTA CAG TCC TCA GGA CTC
 P   E   P   V   T   V   S   W   N   S   G   A   L   T   S   G   V   H   T   F   P   A   V   L   Q   S   S   G   L 183                                                                                                                         211
TAC TCC CTC AGC AGC GTG GTG ACC GTG CCC TCC AGC AGC TTG GGC ACC CAG ACC TAC ATC TGC AAC GTG AAT CAC AAG CCC AGC AAC
 Y   S   L   S   S   V   V   T   V   P   S   S   S   L   G   T   Q   T   Y   I   C   N   V   N   H   K   P   S   N 212                                                         231
ACC AAG GTC GAC AAG AAA GtT GAG CCC AAA TCT TGT GAC AAA ACT CAC ACA TGC CCA CCG TAA
 T   K   V   D   K   K   V   E   P   K   S   C   D   K   T   H   T   C   A   A  Stop
```

Figure 1

Figure 2

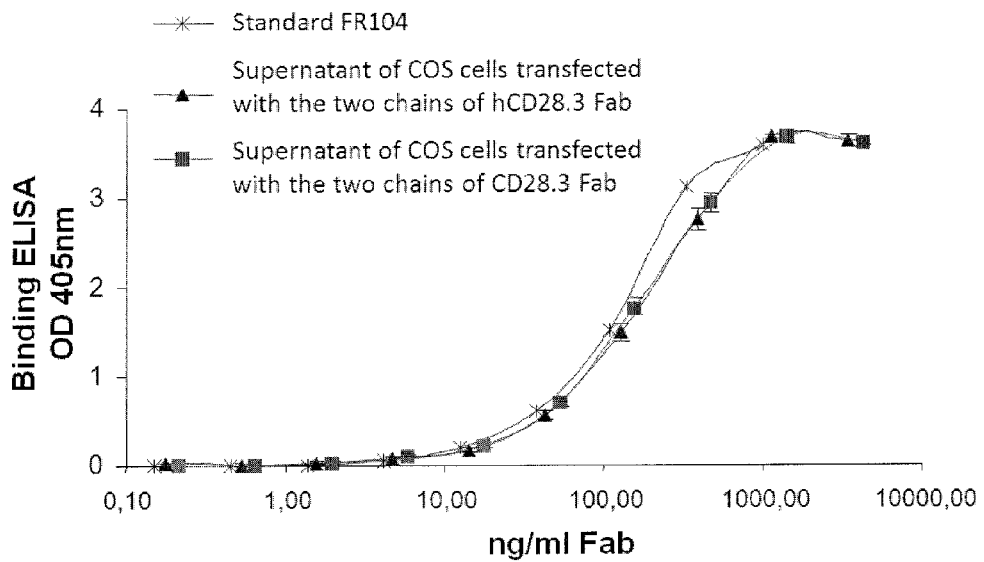
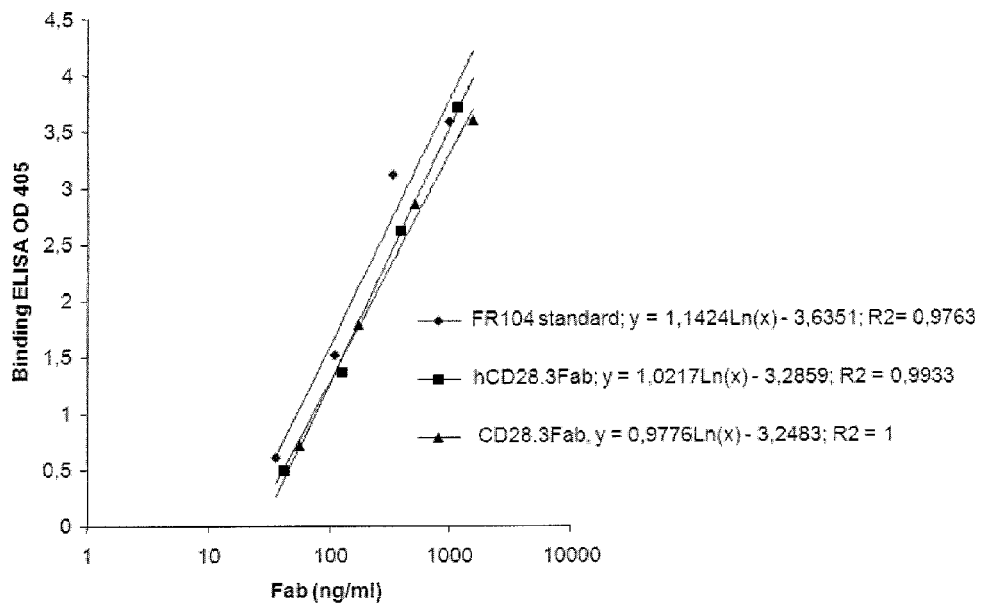
Figure 3

```
   1    ATG GAA TGG TGC TGG GTG TTC CTG TTC CTG CTG TCC GTG ACC GCT    45
   1    Met Glu Trp Cys Trp Val Phe Leu Phe Leu Leu Ser Val Thr Ala    15

46    GGC GTG CAC TCC AAG CAG GTG CAG CTG CAG CAG TCT GGC GCC GAG    90
  16    Gly Val His Ser Lys Gln Val Gln Leu Gln Gln Ser Gly Ala Glu    30

91    CTG AAG AAG CCT GGC GCC TCC GTC AAG GTG TCC TGC AAG GCC TCC   135
  31    Leu Lys Lys Pro Gly Ala Ser Val Lys Val Ser Cys Lys Ala Ser    45

136    GGC TAC ACC TTC ACC GAG TAC ATC ATC CAC TGG ATC AAG CTG AGA   180
  46    Gly Tyr Thr Phe Thr Glu Tyr Ile Ile His Trp Ile Lys Leu Arg    60

181    TCC GGC CAG GGC CTG GAA TGG ATC GGC TGG TTC TAC CCT GGC TCC   225
  61    Ser Gly Gln Gly Leu Glu Trp Ile Gly Trp Phe Tyr Pro Gly Ser    75

226    AAC GAC ATC CAG TAC AAC GCC CAG TTC AAG GGC AAG GCC ACC CTG   270
  76    Asn Asp Ile Gln Tyr Asn Ala Gln Phe Lys Gly Lys Ala Thr Leu    90

271    ACC GCC GAC AAG TCC TCC TCC ACC GTG TAC ATG GAA CTG ACC GGC   315
  91    Thr Ala Asp Lys Ser Ser Ser Thr Val Tyr Met Glu Leu Thr Gly   105

316    CTG ACC CCT GAG GAC TCC GCC GTG TAC TTC TGC GCC AGG CGG GAC   360
 106    Leu Thr Pro Glu Asp Ser Ala Val Tyr Phe Cys Ala Arg Arg Asp   120

361    GAC TTC TCT GGC TAC GAC GCC CTG CCT TAT TGG GGC CAG GGC ACC   405
 121    Asp Phe Ser Gly Tyr Asp Ala Leu Pro Tyr Trp Gly Gln Gly Thr   135

406    CTG GTG ACC GTG TCC GCC GAC AAA ACT CAC ACA TGC CCA CCG TGC   450
 136    Leu Val Thr Val Ser Ala Asp Lys Thr His Thr Cys Pro Pro Cys   150

451    CCA GCA CCT GAG TTC CTG GGG GGA CCA TCA GTC TTC CTG TTC CCC   495
 151    Pro Ala Pro Glu Phe Leu Gly Gly Pro Ser Val Phe Leu Phe Pro   165

496    CCA AAA CCC AAG GAC ACT CTC ATG ATC TCC CGG ACC CCT GAG GTC   540
 166    Pro Lys Pro Lys Asp Thr Leu Met Ile Ser Arg Thr Pro Glu Val   180

541    ACG TGC GTG GTG GTG GAC GTG AGC CAG GAA GAC CCC GAG GTC CAG   585
 181    Thr Cys Val Val Val Asp Val Ser Gln Glu Asp Pro Glu Val Gln   195

586    TTC AAC TGG TAC GTG GAT GGC GTG GAG GTG CAT AAT GCC AAG ACA   630
 196    Phe Asn Trp Tyr Val Asp Gly Val Glu Val His Asn Ala Lys Thr   210

631    AAG CCG CGG GAG GAG CAG TTC AAC AGC ACG TAC CGT GTG GTC AGC   675
 211    Lys Pro Arg Glu Glu Gln Phe Asn Ser Thr Tyr Arg Val Val Ser   225

676    GTC CTC ACC GTC CTG CAC CAG GAC TGG CTG AAC GGC AAG GAG TAC   720
 226    Val Leu Thr Val Leu His Gln Asp Trp Leu Asn Gly Lys Glu Tyr   240

721    AAG TGC AAG GTC TCC AAC AAA GGC CTC CCG TCC TCC ATC GAG AAA   765
 241    Lys Cys Lys Val Ser Asn Lys Gly Leu Pro Ser Ser Ile Glu Lys   255

766    ACC ATC TCC AAA GCC AAA GGG CAG CCC CGA GAG CCA CAG GTG TAC   810
 256    Thr Ile Ser Lys Ala Lys Gly Gln Pro Arg Glu Pro Gln Val Tyr   270

811    ACC CTG CCC CCA TCC CAG GAG GAG ATG ACC AAG AAC CAG GTC AGC   855
 271    Thr Leu Pro Pro Ser Gln Glu Glu Met Thr Lys Asn Gln Val Ser   285

856    CTG ACC TGC CTG GTC AAA GGC TTC TAC CCC AGC GAC ATC GCC GTG   900
 286    Leu Thr Cys Leu Val Lys Gly Phe Tyr Pro Ser Asp Ile Ala Val   300

901    GAG TGG GAG AGC AAT GGG CAG CCG GAG AAC AAC TAC AAG ACC ACG   945
 301    Glu Trp Glu Ser Asn Gly Gln Pro Glu Asn Asn Tyr Lys Thr Thr   315

946    CCT CCC GTG CTG GAC TCC GAC GGC TCC TTC TTC CTC TAC AGC AGG   990
 316    Pro Pro Val Leu Asp Ser Asp Gly Ser Phe Phe Leu Tyr Ser Arg   330

991    CTC ACC GTG GAC AAG AGC AGG TGG CAG GAG GGG AAT GTC TTC TCA  1035
 331    Leu Thr Val Asp Lys Ser Arg Trp Gln Glu Gly Asn Val Phe Ser   345

1036    TGC TCC GTG ATG CAT GAG GCT CTG CAC AAC CAC TAC ACA CAG AAG  1080
 346    Cys Ser Val Met His Glu Ala Leu His Asn His Tyr Thr Gln Lys   360

1081    AGC CTC TCC CTG TCT CTG GGT AAA TGA   1107
 361    Ser Leu Ser Leu Ser Leu Gly Lys End
```

Figure 4

```
1     ATG TCC GTG CCT ACC CAG GTG CTG GGA CTG CTG CTG CTG TGG CTG    45
1     Met Ser Val Pro Thr Gln Val Leu Gly Leu Leu Leu Leu Trp Leu    15

46    ACC GAC GCC AGA TGC GAC ATC CAG ATG ACC CAG TCC CCC TCC TCC    90
16    Thr Asp Ala Arg Cys Asp Ile Gln Met Thr Gln Ser Pro Ser Ser    30

91    CTG TCT GCC TCC GTG GGC GAC CGG GTG ACC ATC ACC TGT AAG ACC    135
31    Leu Ser Ala Ser Val Gly Asp Arg Val Thr Ile Thr Cys Lys Thr    45

136   AAC GAG AAC ATC TAC TCC AAC CTG GCC TGG TAT CAG CAG AAG GAC    180
46    Asn Glu Asn Ile Tyr Ser Asn Leu Ala Trp Tyr Gln Gln Lys Asp    60

181   GGC AAG TCC CCT CAG CTG CTG ATC TAC GCC GCC ACC CAT CTG GTG    225
61    Gly Lys Ser Pro Gln Leu Leu Ile Tyr Ala Ala Thr His Leu Val    75

226   GAG GGC GTG CCC TCT AGA TTC TCC GGC TCC GGC TCT GGC ACC CAG    270
76    Glu Gly Val Pro Ser Arg Phe Ser Gly Ser Gly Ser Gly Thr Gln    90

271   TAC TCC CTG ACC ATC AGC TCC CTG CAG CCT GAG GAC TTC GGC AAC    315
91    Tyr Ser Leu Thr Ile Ser Ser Leu Gln Pro Glu Asp Phe Gly Asn    105

316   TAC TAC TGC CAG CAC TTC TGG GGC ACC CCT TGT ACC TTC GGC GGA    360
106   Tyr Tyr Cys Gln His Phe Trp Gly Thr Pro Cys Thr Phe Gly Gly    120

361   GGC ACC AAG CTG GAA ATC AAG CGG GAC AAA ACT CAC ACA TGC CCA    405
121   Gly Thr Lys Leu Glu Ile Lys Arg Asp Lys Thr His Thr Cys Pro    135

406   CCG TGC CCA GCA CCT GAG TTC CTG GGG GGA CCA TCA GTC TTC CTG    450
136   Pro Cys Pro Ala Pro Glu Phe Leu Gly Gly Pro Ser Val Phe Leu    150

451   TTC CCC CCA AAA CCC AAG GAC ACT CTC ATG ATC TCC CGG ACC CCT    495
151   Phe Pro Pro Lys Pro Lys Asp Thr Leu Met Ile Ser Arg Thr Pro    165

496   GAG GTC ACG TGC GTG GTG GTG GAC GTG AGC CAG GAA GAC CCC GAG    540
166   Glu Val Thr Cys Val Val Val Asp Val Ser Gln Glu Asp Pro Glu    180

541   GTC CAG TTC AAC TGG TAC GTG GAT GGC GTG GAG GTG CAT AAT GCC    585
181   Val Gln Phe Asn Trp Tyr Val Asp Gly Val Glu Val His Asn Ala    195

586   AAG ACA AAG CCG CGG GAG GAG CAG TTC AAC AGC ACG TAC CGT GTG    630
196   Lys Thr Lys Pro Arg Glu Glu Gln Phe Asn Ser Thr Tyr Arg Val    210

631   GTC AGC GTC CTC ACC GTC CTG CAC CAG GAC TGG CTG AAC GGC AAG    675
211   Val Ser Val Leu Thr Val Leu His Gln Asp Trp Leu Asn Gly Lys    225

676   GAG TAC AAG TGC AAG GTC TCC AAC AAA GGC CTC CCG TCC TCC ATC    720
226   Glu Tyr Lys Cys Lys Val Ser Asn Lys Gly Leu Pro Ser Ser Ile    240

721   GAG AAA ACC ATC TCC AAA GCC AAA GGG CAG CCC CGA GAG CCA CAG    765
241   Glu Lys Thr Ile Ser Lys Ala Lys Gly Gln Pro Arg Glu Pro Gln    255

766   GTG TAC ACC CTG CCC CCA TCC CAG GAG GAG ATG ACC AAG AAC CAG    810
256   Val Tyr Thr Leu Pro Pro Ser Gln Glu Glu Met Thr Lys Asn Gln    270

811   GTC AGC CTG ACC TGC CTG GTC AAA GGC TTC TAC CCC AGC GAC ATC    855
271   Val Ser Leu Thr Cys Leu Val Lys Gly Phe Tyr Pro Ser Asp Ile    285

856   GCC GTG GAG TGG GAG AGC AAT GGG CAG CCG GAG AAC AAC TAC AAG    900
286   Ala Val Glu Trp Glu Ser Asn Gly Gln Pro Glu Asn Asn Tyr Lys    300

901   ACC ACG CCT CCC GTG CTG GAC TCC GAC GGC TCC TTC TTC CTC TAC    945
301   Thr Thr Pro Pro Val Leu Asp Ser Asp Gly Ser Phe Phe Leu Tyr    315

946   AGC AGG CTC ACC GTG GAC AAG AGC AGG TGG CAG GAG GGG AAT GTC    990
316   Ser Arg Leu Thr Val Asp Lys Ser Arg Trp Gln Glu Gly Asn Val    330

991   TTC TCA TGC TCC GTG ATG CAT GAG GCT CTG CAC AAC CAC TAC ACA    1035
331   Phe Ser Cys Ser Val Met His Glu Ala Leu His Asn His Tyr Thr    345

1036  CAG AAG AGC CTC TCC CTG TCT CTG GGT AAA TGA    1068
346   Gln Lys Ser Leu Ser Leu Ser Leu Gly Lys End
```

Figure 5

```
   1    ATG GAA TGG TGC TGG GTG TTC CTG TTC CTG CTG TCC GTG ACC GCT    45
   1    Met Glu Trp Cys Trp Val Phe Leu Phe Leu Leu Ser Val Thr Ala    15

46    GGC GTG CAC TCC AAG CAG GTG CAG CTG CAG CAG TCT GGC GCC GAG    90
  16    Gly Val His Ser Lys Gln Val Gln Leu Gln Gln Ser Gly Ala Glu    30

91    CTG AAG AAG CCT GGC GCC TCC GTC AAG GTG TCC TGC AAG GCC TCC   135
  31    Leu Lys Lys Pro Gly Ala Ser Val Lys Val Ser Cys Lys Ala Ser    45

136    GGC TAC ACC TTC ACC GAG TAC ATC ATC CAC TGG ATC AAG CTG AGA   180
  46    Gly Tyr Thr Phe Thr Glu Tyr Ile Ile His Trp Ile Lys Leu Arg    60

181    TCC GGC CAG GGC CTG GAA TGG ATC GGC TGG TTC TAC CCT GGC TCC   225
  61    Ser Gly Gln Gly Leu Glu Trp Ile Gly Trp Phe Tyr Pro Gly Ser    75

226    AAC GAC ATC CAG TAC AAC GCC CAG TTC AAG GGC AAG GCC ACC CTG   270
  76    Asn Asp Ile Gln Tyr Asn Ala Gln Phe Lys Gly Lys Ala Thr Leu    90

271    ACC GCC GAC AAG TCC TCC TCC ACC GTG TAC ATG GAA CTG ACC GGC   315
  91    Thr Ala Asp Lys Ser Ser Ser Thr Val Tyr Met Glu Leu Thr Gly   105

316    CTG ACC CCT GAG GAC TCC GCC GTC TAC TTC TGC GCC AGG CGG GAC   360
 106    Leu Thr Pro Glu Asp Ser Ala Val Tyr Phe Cys Ala Arg Arg Asp   120

361    GAC TTC TCT GGC TAC GAC GCC CTG CCT TAT TGG GGC CAG GGC ACC   405
 121    Asp Phe Ser Gly Tyr Asp Ala Leu Pro Tyr Trp Gly Gln Gly Thr   135

406    CTG GTG ACC GTG TCC GCC GAG CCC AAA TCT TGT GAC AAA ACT CAC   450
 136    Leu Val Thr Val Ser Ala Glu Pro Lys Ser Cys Asp Lys Thr His   150

451    ACA TGC CCA CCG TGC CCA GCA CCT GAG TTC CTG GGG GGA CCA TCA   495
 151    Thr Cys Pro Pro Cys Pro Ala Pro Glu Phe Leu Gly Gly Pro Ser   165

496    GTC TTC CTG TTC CCC CCA AAA CCC AAG GAC ACT CTC ATG ATC TCC   540
 166    Val Phe Leu Phe Pro Pro Lys Pro Lys Asp Thr Leu Met Ile Ser   180

541    CGG ACC CCT GAG GTC ACG TGC GTG GTG CTG GAC GTG AGC CAG GAA   585
 181    Arg Thr Pro Glu Val Thr Cys Val Val Val Asp Val Ser Gln Glu   195

586    GAC CCC GAG GTC CAG TTC AAC TGG TAC GTG GAT GGC GTG GAG GTG   630
 196    Asp Pro Glu Val Gln Phe Asn Trp Tyr Val Asp Gly Val Glu Val   210

631    CAT AAT GCC AAG ACA AAG CCG CGG GAG GAG CAG TTC AAC AGC ACG   675
 211    His Asn Ala Lys Thr Lys Pro Arg Glu Glu Gln Phe Asn Ser Thr   225

676    TAC CGT GTG GTC AGC GTC CTC ACC GTC CTG CAC CAG GAC TGG CTG   720
 226    Tyr Arg Val Val Ser Val Leu Thr Val Leu His Gln Asp Trp Leu   240

721    AAC GGC AAG GAG TAC AAG TGC AAG GTC TCC AAC AAA GCC CTC CCG   765
 241    Asn Gly Lys Glu Tyr Lys Cys Lys Val Ser Asn Lys Gly Leu Pro   255

766    TCC TCC ATC GAG AAA ACC ATC TCC AAA GCC AAA GGG CAG CCC CGA   810
 256    Ser Ser Ile Glu Lys Thr Ile Ser Lys Ala Lys Gly Gln Pro Arg   270

811    GAG CCA CAG GTG TAC ACC CTG CCC CCA TCC CAG GAG GAG ATG ACC   855
 271    Glu Pro Gln Val Tyr Thr Leu Pro Pro Ser Gln Glu Glu Met Thr   285

856    AAG AAC CAG GTC AGC CTG ACC TGC CTG GTC AAA GGC TTC TAC CCC   900
 286    Lys Asn Gln Val Ser Leu Thr Cys Leu Val Lys Gly Phe Tyr Pro   300

901    AGC GAC ATC GCC GTG GAG TGG GAG AGC AAT GGG CAG CCG GAG AAC   945
 301    Ser Asp Ile Ala Val Glu Trp Glu Ser Asn Gly Gln Pro Glu Asn   315

946    AAC TAC AAG ACC ACG CCT CCC GTG CTG GAC TCC GAC GGC TCC TTC   990
 316    Asn Tyr Lys Thr Thr Pro Pro Val Leu Asp Ser Asp Gly Ser Phe   330

991    TTC CTC TAC AGC AGG CTC ACC GTG GAC AAG AGC AGG TGG CAG GAG  1035
 331    Phe Leu Tyr Ser Arg Leu Thr Val Asp Lys Ser Arg Trp Gln Glu   345

1036    GGG AAT GTC TTC TCA TGC TCC GTG ATG CAT GAG GCT CTG CAC AAC  1080
 346    Gly Asn Val Phe Ser Cys Ser Val Met His Glu Ala Leu His Asn   360

1081    CAC TAC ACA CAG AAG AGC CTC TCC CTG TCT CTG GGT AAA TGA      1122
 361    His Tyr Thr Gln Lys Ser Leu Ser Leu Ser Leu Gly Lys End
```

Figure 6

```
   1    ATG TCC GTG CCT ACC CAG GTG CTG GGA CTG CTG CTG CTG TGG CTG    45
   1    Met Ser Val Pro Thr Gln Val Leu Gly Leu Leu Leu Leu Trp Leu    15

46    ACC GAC GCC AGA TGC GAC ATC CAG ATG ACC CAG TCC CCC TCC TCC    90
  16    Thr Asp Ala Arg Cys Asp Ile Gln Met Thr Gln Ser Pro Ser Ser    30

91    CTG TCT GCC TCC GTG GGC GAC CGG GTG ACC ATC ACC TGT AAG ACC   135
  31    Leu Ser Ala Ser Val Gly Asp Arg Val Thr Ile Thr Cys Lys Thr    45

136    AAC GAG AAC ATC TAC TCC AAC CTG GCC TGG TAT CAG CAG AAG GAC   180
  46    Asn Glu Asn Ile Tyr Ser Asn Leu Ala Trp Tyr Gln Gln Lys Asp    60

181    GGC AAG TCC CCT CAG CTG CTG ATC TAC GCC GCC ACC CAT CTG GTG   225
  61    Gly Lys Ser Pro Gln Leu Leu Ile Tyr Ala Ala Thr His Leu Val    75

226    GAG GGC GTG CCC TCT AGA TTC TCC GGC TCC GGC TCT GGC ACC CAG   270
  76    Glu Gly Val Pro Ser Arg Phe Ser Gly Ser Gly Ser Gly Thr Gln    90

271    TAC TCC CTG ACC ATC AGC TCC CTG CAG CCT GAG GAC TTC GGC AAC   315
  91    Tyr Ser Leu Thr Ile Ser Ser Leu Gln Pro Glu Asp Phe Gly Asn   105

316    TAC TAC TGC CAG CAC TTC TGG GGC ACC CCT TGT ACC TTC GGC GGA   360
 106    Tyr Tyr Cys Gln His Phe Trp Gly Thr Pro Cys Thr Phe Gly Gly   120

361    GGC ACC AAG CTG GAA ATC AAG CGG GAG CCC AAA TCT TGT GAC AAA   405
 121    Gly Thr Lys Leu Glu Ile Lys Arg Glu Pro Lys Ser Cys Asp Lys   135

406    ACT CAC ACA TGC CCA CCG TGC CCA GCA CCT GAG TTC CTG GGG GGA   450
 136    Thr His Thr Cys Pro Pro Cys Pro Ala Pro Glu Phe Leu Gly Gly   150

451    CCA TCA GTC TTC CTG TTC CCC CCA AAA CCC AAG GAC ACT CTC ATG   495
 151    Pro Ser Val Phe Leu Phe Pro Pro Lys Pro Lys Asp Thr Leu Met   165

496    ATC TCC CGG ACC CCT GAG GTC ACG TGC GTG GTG GTG GAC GTG AGC   540
 166    Ile Ser Arg Thr Pro Glu Val Thr Cys Val Val Val Asp Val Ser   180

541    CAG GAA GAC CCC GAG GTC CAG TTC AAC TGG TAC GTG GAT GGC GTG   585
 181    Gln Glu Asp Pro Glu Val Gln Phe Asn Trp Tyr Val Asp Gly Val   195

586    GAG GTG CAT AAT GCC AAG ACA AAG CCG CGG GAG GAG CAG TTC AAC   630
 196    Glu Val His Asn Ala Lys Thr Lys Pro Arg Glu Glu Gln Phe Asn   210

631    AGC ACG TAC CGT GTG GTC AGC GTC CTC ACC GTC CTG CAC CAG GAC   675
 211    Ser Thr Tyr Arg Val Val Ser Val Leu Thr Val Leu His Gln Asp   225

676    TGG CTG AAC GGC AAG GAG TAC AAG TGC AAG GTC TCC AAC AAA GGC   720
 226    Trp Leu Asn Gly Lys Glu Tyr Lys Cys Lys Val Ser Asn Lys Gly   240

721    CTC CCG TCC TCC ATC GAG AAA ACC ATC TCC AAA GCC AAA GGG CAG   765
 241    Leu Pro Ser Ser Ile Glu Lys Thr Ile Ser Lys Ala Lys Gly Gln   255

766    CCC CGA GAG CCA CAG GTG TAC ACC CTG CCC CCA TCC CAG GAG GAG   810
 256    Pro Arg Glu Pro Gln Val Tyr Thr Leu Pro Pro Ser Gln Glu Glu   270

811    ATG ACC AAG AAC CAG GTC AGC CTG ACC TGC CTG GTC AAA GGC TTC   855
 271    Met Thr Lys Asn Gln Val Ser Leu Thr Cys Leu Val Lys Gly Phe   285

856    TAC CCC AGC GAC ATC GCC GTG GAG TGG GAG AGC AAT GGG CAG CCG   900
 286    Tyr Pro Ser Asp Ile Ala Val Glu Trp Glu Ser Asn Gly Gln Pro   300

901    GAG AAC AAC TAC AAG ACC ACG CCT CCC GTG CTG GAC TCC GAC GGC   945
 301    Glu Asn Asn Tyr Lys Thr Thr Pro Pro Val Leu Asp Ser Asp Gly   315

946    TCC TTC TTC CTC TAC AGC AGG CTC ACC GTG GAC AAG AGC AGG TGG   990
 316    Ser Phe Phe Leu Tyr Ser Arg Leu Thr Val Asp Lys Ser Arg Trp   330

991    CAG GAG GGG AAT GTC TTC TCA TGC TCC GTG ATG CAT GAG GCT CTG  1035
 331    Gln Glu Gly Asn Val Phe Ser Cys Ser Val Met His Glu Ala Leu   345

1036    CAC AAC CAC TAC ACA CAG AAG AGC CTC TCC CTG TCT CTG GGT AAA  1080
 346    His Asn His Tyr Thr Gln Lys Ser Leu Ser Leu Ser Leu Gly Lys   360

1081    TGA    1083
 361    End
```

Figure 7

ANTI-CD28 HUMANIZED ANTIBODIES

RELATED APPLICATIONS

The present application is a U.S. National Phase Application of International Application No. PCT/IB2011/050646 (filed Feb. 16, 2011) which claims priority to European Application Nos. 10290080.0 (filed Feb. 18, 2010) and 10290389.5 (filed Jul. 13, 2010) which are hereby incorporated by reference in their entirety.

SEQUENCE LISTING SUBMISSION VIA EFS-WEB

A computer readable text file, entitled "045636-5202_SequenceListing.txt," created on or about Jan. 12, 2014, with a file size of about 36 kb contains the sequence listing for this application and is hereby incorporated by reference in its entirety.

The present invention relates to humanized antibodies binding CD28, to monovalent fragments thereof, and to their therapeutic uses, in particular in the context of regulating T cell activation.

Abnormal activation of T cells is involved in the pathogenesis of many autoimmune diseases, and also in transplant rejection phenomena, where they cause an immune response directed against the transplanted organ to develop.

One of the most important systems for regulating T lymphocyte activation is the molecular system B7/CD28/CTLA4. This system plays, for example, an essential role in the mechanisms of transplant rejection (WOODWARD et al., Transplantation, 66, 14-20, 1998). The molecules B7.1 (CD80) and B7.2 (CD86) borne by the APCs can activate the receptor CD28 and also the receptor CTLA4 of T lymphocytes. The activation of CD28 sends the T lymphocyte a positive signal which stimulates the cell; on the other hand, the activation of CTLA4 sends a negative signal which leads to a non-response (anergy) (FALLARINO et al., J. Exp. Med., 188, 205-210, 1998).

Resting T lymphocytes express a large amount of CD28 and very little CTLA4. When there is a first cognitive contact between an APC and a T lymphocyte, the CD28/B7 interaction is favored, which activates the cell. It is only several hours after the initiation of activation that, due to the increase in membrane expression of CTLA4, the affinity of which for B7 is 5 to 10 times greater than that of CD28, the B7/CD28 interaction shifts in favor of a B7/CTLA4 interaction.

Regulatory T lymphocytes express a large amount of CD28 and of CTLA4 that prevent or allow, respectively, the suppressive activity of regulatory T lymphocytes. In the presence of APC expressing high level of B7, the CD28/B7 interaction prevents the suppressive activity of regulatory T lymphocytes (Sansom et al., Trends Immunol. 24, 314-319, 2003).

Selective inhibition of the agonist signal given to the T cell by CD28, leaving the antagonist system consisting of the pair CTLA4/B7 intact, via specific blocking of the CD28/B7 interaction, would make it possible to prevent T lymphocyte activation and to promote immune suppression by regulatory T lymphocytes. Such specific blocking of the CD28/B7 interaction can be obtained using some antibodies directed against CD28.

These antibodies are to be used in a monovalent form (for instance as Fab or scFv fragments), since when used in their divalent native form, their binding to CD28 brings about the dimerization and the activation of this receptor. Fab fragments each contain a light chain and the first half of a heavy chain; scFv fragments consist of the variable portions of the heavy and light chains of a parent antibody, connected to one another via a flexible linker (CLACKSON et al., Nature, 352, 624-628, 1991), thus forming a single-chain protein.

One such antibody is antibody CD28.3, produced by the hybridoma cell line CNCM I-2582, and disclosed in PCT application WO 02/051871. This antibody, when used in a monovalent form such as scFv fragments, is capable of blocking in vitro the CD28 receptor without activating it (PCT WO 02/051871; VANHOVE et al., Blood, 102, 564-70, 2003), and has shown also its efficiency in vivo in models of organ transplantation in mice and in primates (POIRIER et al., World Transplant Congress, Sydney, Australia. Aug. 16-21, 2008; POIRIER et al, Sci Trans Med, 2:17, p17ra10, 2010).

A drawback of all monoclonal antibodies derived from murine sources, is their immunogenicity when administered to human subjects. They provoke anti-mouse immune response, which results in a lesser efficiency of the treatment, in particular when repeated administration is required.

This drawback can, in principle, be avoided by the use of humanized antibodies. The aim of humanization is to obtain a recombinant antibody which has similar antigen-binding properties as the mouse monoclonal antibody from which the complementarity-determining regions (CDRs) sequences were derived, and which is far less immunogenic in humans.

The CDRs are the portions of the variable domains of an antibody which directly contact the antigen and determine the antigen-binding specificity; the framework regions (FRs) which are located between the CDRs in the variable domains do not directly contact the antigen, but serves as a scaffold to maintain the global structure of the variable domains.

Several approaches to antibody humanization have been reported. The more widely used are based on "CDR grafting", which involves the transplantation of the CDRs of a murine antibody into appropriate human FRs. However, in many antibodies, some FR residues are important for antigen binding, because they influence the conformation of CDRs and thus their antigen binding properties, in particular the binding affinity. A loss in binding affinity is particularly detrimental in the case of an antibody intended to be used in a monovalent form which generally exhibit less affinity for the antigen than the native divalent antibody. Thus, in most cases, it is further necessary, in order to obtain a sufficient binding affinity, to reintroduce one or several framework residues from the mouse antibody in the human FRs, with the risk of simultaneously bringing back unwanted immunogenicity.

Another approach to antibody humanisation, called "de-immunization", involves the identification within the FRs regions of the antibody, of B-cell and T-cell epitopes recognized as "foreign" and therefore potentially immunogenic in humans, and to remove them by appropriate amino-acids substitutions. This approach however also entails the risk that FR residues important for antigen binding are deleted. Moreover, some immunogenic epitopes may lie in the CDRs and trying to remove them involves a very high risk of destroying not only the antigen-binding affinity but also the antigen-binding specificity of the antibody.

Therefore, a major issue in antibody humanisation is to determine which amino acid residues are critical for retaining the antigen-binding properties. Various methods have been proposed for predicting the more appropriate sites for substitution in the FRs regions. Although they provide general principles that may be of some help in the first steps of humanization, the final result greatly varies from an antibody to another. Thus, for a given antibody, it is very difficult to foretell which substitutions will provide the desired result. In the case wherein not only substitutions in the FRs, but also in the CDRs would be necessary to decrease satisfactorily the immunogenicity in humans, the final result becomes totally unpredictable.

The inventors have succeeded in producing humanized CD28.3 (hereinafter referred to as hCD28.3), with a low immunogenicity, and which, although it has several amino-acids substitutions including a non-conservative K→Q substitution in the CDR2 of the heavy chain, retains the CD28 binding properties of the parent mouse CD28.3. When used in a monovalent form, the hCD28.3 of the invention also retains the CD28 binding properties of the parent mouse CD28.3.

The present invention provides an anti-CD28 antibody, characterised in that it is selected among:

a) an antibody having a CD28-binding site consisting of:
a first variable domain (also defined herein as the "heavy chain variable domain") defined by the following sequence:
VQLQQSGAELKKPGASVKVSCKASGYT-FTEYIIHWIKLRSGQGLEWI GWFYPG-SNDIQYNAQFKGKATL-TADKSSSTVYMELTGLTPEDSAVYFCARRDDFSG YDALPYWGQGTLVTVSA (SEQ ID NO: 1), wherein said variable domain may optionally further comprise a Q residue at its N-terminal end;
a second variable domain (also defined herein as the "light chain variable domain") defined by the following sequence:
DIQMTQSPSSLSASVGDRVTITCKT-NENIYSNLAWYQQKDGKSPQLL IYAATHLVEG-VPSRFSGSGSGTQYSLTISSLQPEDF-GNYYCQHFWGTPXTFGGGTKLEI KR (SEQ ID NO: 2), wherein X=C, A, or N.

b) an antibody having a CD28-binding site consisting of:
a first variable domain having the CDRs of the variable domain of SEQ ID NO: 1;
a second variable domain having the CDRs of the variable domain of SEQ ID NO: 2.

The term "anti-CD28 antibody" herein refers to any antigen-binding protein having at least one antigen-binding site (consisting of the variable domains of the light chain and of the heavy chain) able to specifically bind human CD28. It encompasses antibodies in a divalent form (such as native immunoglobulin molecules or F(ab)'₂ fragments) with two CD28-binding sites, as well as antibodies in a monovalent form which have a single CD28-binding site, (for instance Fab, Fab', Fv and scFv fragments). In most cases, antibodies in a monovalent form will be preferred.

It includes in particular recombinant antibodies comprising a CD28-binding site associated with one or more heterologous polypeptide(s).

By way of example, an antibody of the invention may be a recombinant Fab or Fab' fragment containing the constant domain CH1 of a human immunoglobulin fused at the C-terminal end of the variable domain of SEQ ID NO: 1, and the constant domain CL of a human immunoglobulin fused at the C-terminal end of the variable domain of SEQ ID NO: 2. An example of such a recombinant Fab fragment is a Fab fragment with a heavy chain having the sequence of amino-acids 21-251 of SEQ ID NO: 4 and a light chain having the sequence of amino-acids 21-234 of SEQ ID NO: 6.

Also, a hCD28.3 antibody of the invention may comprise, besides the variable domains of SEQ ID NO: 1 and SEQ ID NO: 2, defined above, one or more of the following components:
a human constant region (Fc). This constant region can be selected among constant domains from any class of immunoglobulins, including IgM, IgG, IgD, IgA and IgE, and any isotype, including IgG1, IgG2, IgG3 and IgG4. Preferred constant regions are selected among constant domains of IgG, in particular IgG4.
a protein which makes it possible to prolong the plasma half-life when it is administered in vivo under monovalent form as disclosed for instance in PCT WO 02/051871; in a preferred embodiment, said protein is the CH2-CH3 domains of an IgG molecule, as disclosed in PCT/IB/2010/000196; according to said embodiment, a hCD28.3 monovalent antibody of the invention is an heterodimer of:
a first protein chain consisting essentially of, from its N-terminus to its C-terminus:
a region A having the sequence SEQ ID NO: 1;
a region B consisting of a peptide linker and the CH2 and CH3 domains of an IgG immunoglobulin;
a second protein chain consisting essentially of, from its N-terminus to its C-terminus:
a region A' having the sequence SEQ ID NO: 2;
a region B identical to the region B of the first polypeptide.

Preferably, the peptide linker is the hinge region of human IgG1 immunoglobulins having the sequence EPKSCDKTH-TCPPCP (SEQ ID NO: 7), and the CH2 and CH3 domains are those of an immunoglobulin of the IgG4 subclass. One can also use a shortened version of said hinge region, having the sequence DKTHTCPPCP (SEQ ID NO: 8).

According to a preferred embodiment, the polypeptide sequence of the first protein chain is the sequence of amino-acids 21-368 of SEQ ID NO: 10, and the polypeptide sequence of the second protein chain is the sequence of amino-acids 21-355 of SEQ ID NO: 12. According to another preferred embodiment, the polypeptide sequence of the first protein chain is the sequence of amino-acids 21-373 of SEQ ID NO: 14, and the polypeptide sequence of the second protein chain is the sequence of amino-acids 21-360 of SEQ ID NO: 16.

Optionally, a hCD28.3 antibody of the invention may further comprise one or more of the following components:
a protein having pharmacological activity (for example a toxin);
one or more tag polypeptide(s).

Alternatively, to prolong their plasma half life, in particular when they are under the form of Fab fragments, the antibodies of the invention can be conjugated with water soluble polymers such as polyethylene glycol (PEGylation). PEGylation is a classical way to enhance the pharmacokinetic properties of therapeutic polypeptides, and can be achieved by techniques known in the art.

In this respect, the inventors found that the replacement of the original cysteine residue at position 96 of the variable domain of the native CD 28.3 by an alanine or an asparagine residue (resulting in an antibody having a light chain containing a variable domain of SEQ ID NO: 2 wherein X=A or N) allowed a better efficacy in pegylation of the antibody using maleimide-activated polyethylene glycol (targeting reactive cystein residues), without modifying substantially its binding activity, although cysteine-96 is comprised in the CDR3 of the antibody light chain. The benefit of the replacement of the original cysteine residue at position 96 of the variable domain mainly consist in a specific branching of the polyethylene glycol onto the C-terminal cysteine residue of the heavy chain. Without replacement of the original cysteine residue at position 96 of the variable domain of the native CD 28.3, maleimide-activated polyethylene glycol can bind to that cysteine residue and impair the binding activity of the Fab molecule.

The inventors also found that addition of a di-alanine extension after the C-terminal cysteine of the heavy chain also resulted in a better pegylation efficiency.

The invention also encompasses a polynucleotide selected among:

a) a polynucleotide encoding a polypeptide having the CDRs of SEQ ID NO: 1, in particular a polynucleotide encoding a polypeptide of SEQ ID NO: 1;

b) a polynucleotide encoding a polypeptide having the CDRs of SEQ ID NO: 2, in particular a polynucleotide encoding a polypeptide of SEQ ID NO: 2;

c) a polynucleotide encoding an hCD28.3 antibody of the invention, as defined above.

Polynucleotides of the invention generally also comprise additional sequences: for instance they may advantageously comprise a sequence encoding a leader sequence or signal peptide allowing secretion of said protein chain.

The present invention also encompasses recombinant vectors, in particular expression vectors, comprising a polynucleotide of the invention, associated with transcription- and translation-controlling elements which are active in the host cell chosen. Vectors which can be used to construct expression vectors in accordance with the invention are known in themselves, and will be chosen in particular as a function of the host cell intended to be used.

The present invention also encompasses host-cells transformed with a polynucleotide of the invention. Preferably, said host cell is transformed with a polynucleotide comprising a sequence encoding the heavy chain of a hCD28.3 antibody of the invention and a polynucleotide comprising a sequence encoding the light chain of a hCD28.3 antibody of the invention, and expresses said antibody. Said polynucleotides can be inserted in the same expression vector, or in two separate expression vectors.

Host cells which can be used in the context of the present invention can be prokaryotic or eukaryotic cells. Among the eukaryotic cells which can be used, mention will in particular be made of plant cells, cells from yeast, such as Saccharomyces, insect cells, such as Drosophila or Spodoptera cells, and mammalian cells such as HeLa, CHO, 3T3, C127, BHK, COS, etc., cells.

The construction of expression vectors of the invention and the transformation of the host cells can be carried out by the conventional techniques of molecular biology.

Still another objet of the invention is a method for preparing a hCD28.3 antibody of the invention. Said method comprises culturing a host-cell transformed with a polynucleotide comprising a sequence encoding the heavy chain of a hCD28.3 antibody of the invention and a polynucleotide comprising a sequence encoding the light chain of a hCD28.3 antibody of the invention and recovering said antibody from said culture.

If the antibody is secreted by the host-cell, it can be recovered directly from the culture medium; if not, cell lysis will be carried out beforehand. The antibody can then be purified from the culture medium or from the cell lysate, by conventional procedures, known in themselves to those skilled in the art, for example by fractionated precipitation, in particular precipitation with ammonium sulfate, electrophoresis, gel filtration, affinity chromatography, etc.

The hCD28.3 antibodies of the invention can be used to obtain medicinal products. These medicinal products are also part of the object of the invention.

The present invention also comprises a therapeutic composition comprising a hCD28.3 antibody of the invention, together with a pharmaceutically acceptable excipient.

Preferably, said composition is a composition for parenteral administration, formulated to allow the administration of a dose of from 0.5 to 20 mg/Kg, advantageously of from 5 to 10 mg/Kg of an hCD28.3 antibody of the invention. The injection route of the composition can be preferably sub-cutaneous or intra-venous.

For instance, hCD28.3 antibodies of the invention can be used to obtain immunosuppressant medicinal products which selectively blocks T cell activation phenomena involving the CD28 receptor. Such immunosuppressant medicinal products which act by selective blocking of CD28 have applications in all T lymphocyte-dependent pathological conditions, including in particular transplant rejection, graft-versus-host disease, T lymphocyte-mediated autoimmune diseases, such as type I diabetes, rheumatoid arthritis or multiple sclerosis, and type IV hypersensitivity, which is involved in allergic phenomena and also in the pathogenesis of chronic inflammatory diseases, in particular following infection with a pathogenic agent (in particular leprosy, tuberculosis, leishmaniasis, listeriosis, etc.).

The present invention will be understood more clearly from the further description which follows, which refers to nonlimiting examples of the preparation and properties of a hCD28.3 antibody in accordance with the invention.

The construction of expression vectors of the invention and the transformation of host-cells can be made by the standard techniques of molecular biology.

A hCD28.3 antibody of the invention can be obtained by culturing a host cell containing an expression vector comprising a nucleic acid sequence encoding said antibody, under conditions suitable for the expression thereof, and recovering said antibody from the host cell culture.

The present invention will be further illustrated by the following additional description, which refers to examples illustrating the properties of hCD28.3 antibodies of the invention. It should be understood however that these examples are given only by way of illustration of the invention and do not constitute in any way a limitation thereof.

LEGENDS OF THE DRAWINGS

FIG. 1: Nucleotidic (SEQ ID NO: 3) and amino acid (SEQ ID NO: 4) sequences of the Signal-VH-hCH1 construction. Bold: leader sequence (Nucleotide, SEQ ID NO: 17; amino acid, SEQ ID NO: 18); Underlined: positions of the CDRs (SEQ ID NO: 19, 20 and 21) of the parent CD28.3 antibody. Italics: human CH1 region (Nucleotide, SEQ ID NO: 22; amino acid, SEQ ID NO: 23); Highlighted and double underlined: substitutions made in the CD28.3 antibody VH region.

Figure 2:
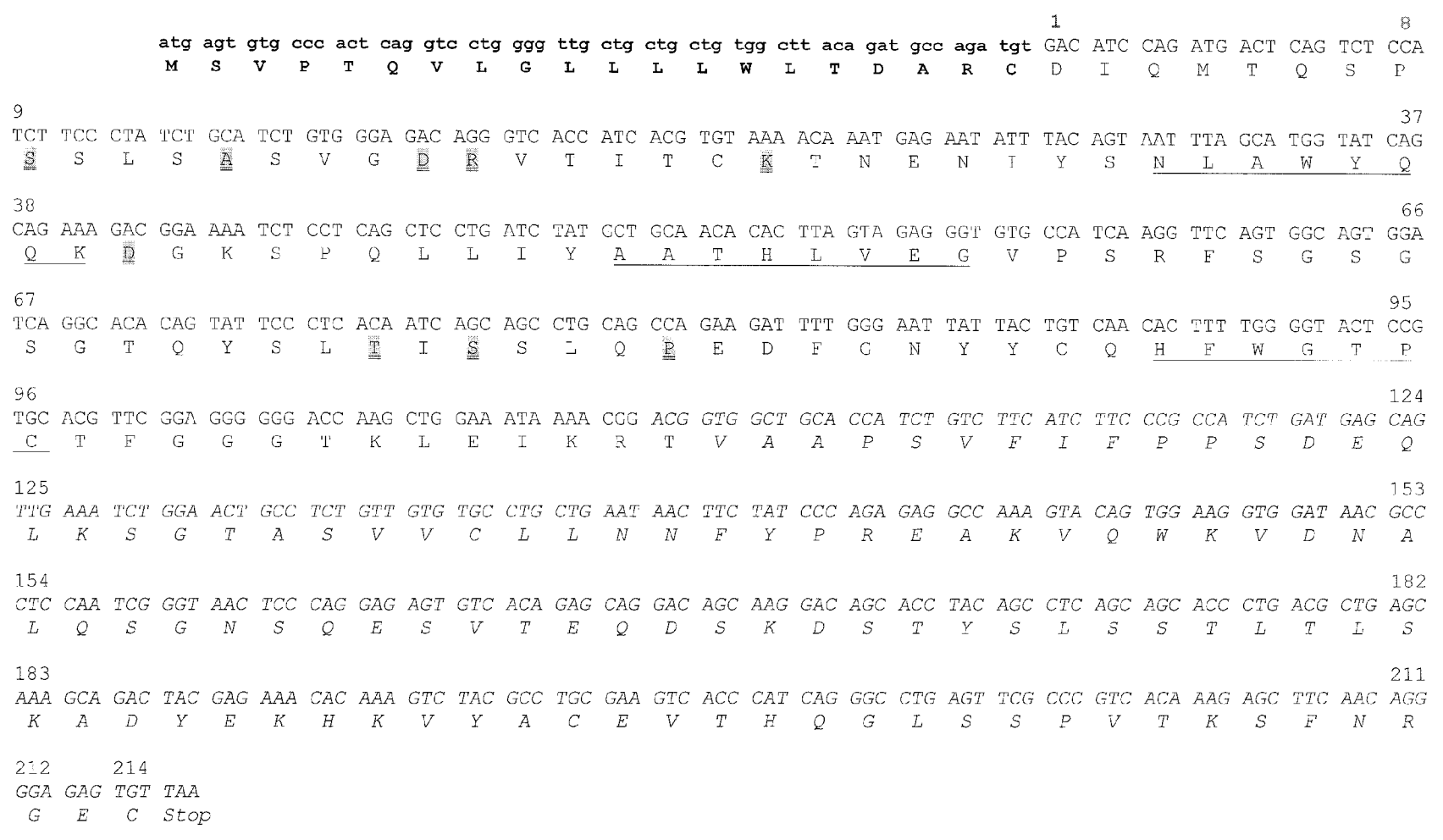

FIG. 2: Nucleotidic (SEQ ID NO: 5) and amino acid (SEQ ID NO: 6) sequences of the Signal-VL-hCκ construction. Bold: leader sequence (Nucleotide, SEQ ID NO: 24; amino acid, SEQ ID NO: 25); Underlined: positions of the CDRs (SEQ ID NO: 26, 27, and 28) of the parent CD28.3 antibody. Italics: human c kappa region (Nucleotide, SEQ ID NO: 29; amino acid, SEQ ID NO: 30); Highlighted and double underlined: substitutions made in the CD28.3 antibody VL region.

FIG. 3: A) optical density at 405 nm for increasing concentrations of FR104, hCD28.3 Fab or CD28.3 Fab in the Binding ELISA; B) calculation of the regression curves, allowing for determining comparative AC50 values.

FIG. 4: Nucleotidic (SEQ ID NO: 9) and amino acid (SEQ ID NO: 10) sequences of the hVHCD28.3-short hingeγ1-hγ4CH2CH3 construction. Bold: leader sequence (SEQ ID NO: 18). Underlined: CDRs (SEQ ID NO: 19, 20, and 21).

Double underlined: hinge region (SEQ ID NO: 8). Dotted underlined: CH2-CH3 domains (SEQ ID NO: 31) of the human IgG4.

FIG. 5: Nucleotidic (SEQ ID NO: 11) and amino acid (SEQ ID NO: 12) sequences of the hVLCD28.3-short hingeγ1-hγ4CH2CH3 construction. Bold: leader sequence (SEQ ID NO: 25). Underlined: CDRs (SEQ ID NO: 26, 27 and 28). Double underlined: hinge region (SEQ ID NO: 8). Dotted underlined: CH2-CH3 domains (SEQ ID NO: 31) of the human IgG4.

FIG. 6: Nucleotidic (SEQ ID NO: 13) and amino acid (SEQ ID NO: 14) sequences of the hVHCD28.3-full hingeγ1-hγ4CH2CH3 construction. Bold: leader sequence (SEQ ID NO: 18). Underlined: CDRs (SEQ ID NO: 19, 20, and 21). Double underlined: hinge region (SEQ ID NO: 7). Dotted underlined: CH2-CH3 domains (SEQ ID NO: 31) of the human IgG1.

FIG. 7: Nucleotidic (SEQ ID NO: 15) and amino acid (SEQ ID NO: 16) sequences of the hVLCD28.3-full hingeγ1-hγ4CH2CH3 construction. Bold: leader sequence (SEQ ID NO: 25). Underlined: CDRs (SEQ ID NO: 26, 27 and 28). Double underlined: hinge region (SEQ ID NO: 7). Dotted underlined: CH2-CH3 domains (SEQ ID NO: 31) of the human IgG1.

FIG. 8: Anti-CD28 binding properties of hVH/VL CD28.3 monovalent antibodies. COS cells were co-transfected with 2 μg (each) pSignal-hVH-short hingeγ1-hγ4CH2-CH3 and pSignal-hVL-short hingeγ1-hγ4CH2-CH3, or co-transfected with 2 μg (each) pSignal-hVH-full hingeγ1-hγ4CH2-CH3 and pSignal-hVL-full hingeγ1-hγ4CH2-CH3. After 6 days, supernatants were collected and monovalent antibodies were dosed using a first sandwich ELISA. Supernatants were also assessed with a binding ELISA on immobilized CD28 target molecules and bound monovalent anti-CD28 antibodies were revealed with anti-human Fc antibodies labeled with peroxidase. A: Optical density obtained with indicated molecules according to their concentration. B: table with regression curves and the calculation of ED50 (effective dose 50), the concentration needed to reach 50% binding activity in this assay.

Figure 9:
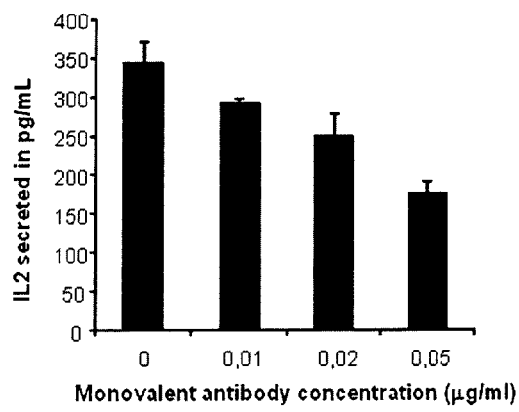

FIG. 9: hVH/VL CD28.3 monovalent antibodies inhibit IL-2 secretion by activated T cells. Jurkat T cells were stimulated with SEE superantigen and Raji antigen-presenting-cells during 48 h, in the presence of indicated concentrations of purified hVH/VL-short hingeγ1-hγ4CH2-CH3 monovalent antibodies. Supernatant were collected and IL-2 measured by ELISA.

Figure 10:
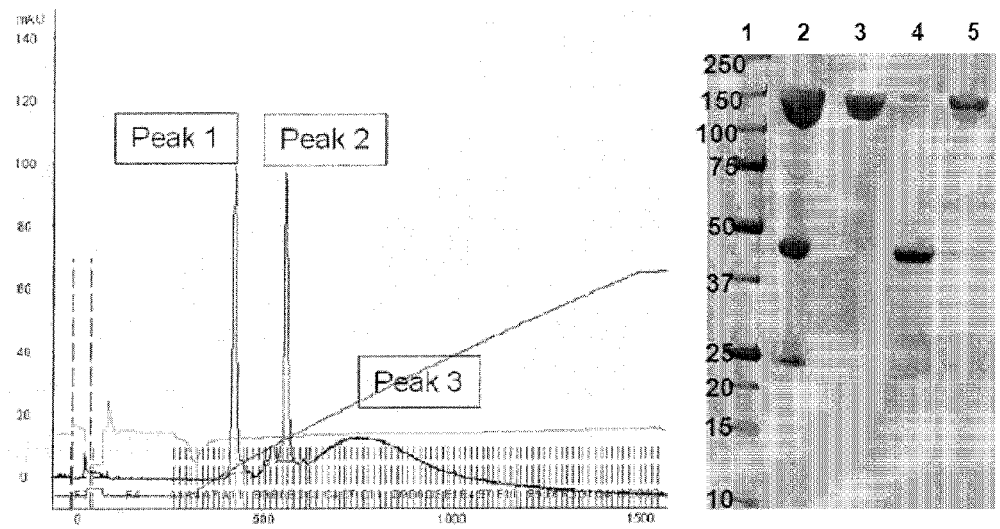

FIG. 10: SP sepharose HP-chromatography (left) and SDS-PAGE (right) under unreduced conditions after pegylation of C96-Fabs from humanised CD28.3 antibody. Lane 1: marker; lane 2:load; lane 3: Peak 1; lane 4: Peak 2; lane 5: Peak 3.

Figure 11:
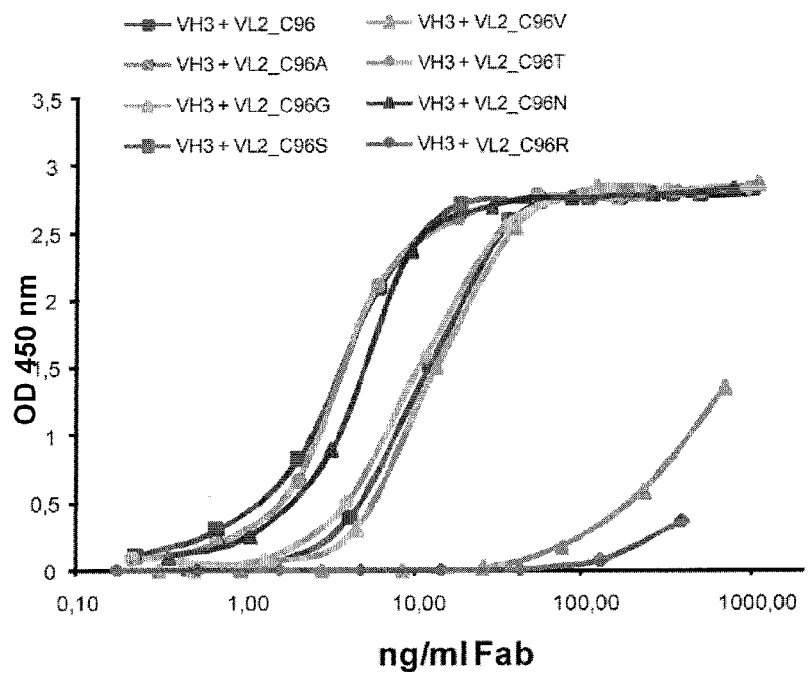

FIG. 11: Binding properties for CD28 of recombinant hCD28.3 Fabs with or without C96 mutations. The graph shows binding activity (Y axis) according to Fab concentration (X axis).

Figure 12:
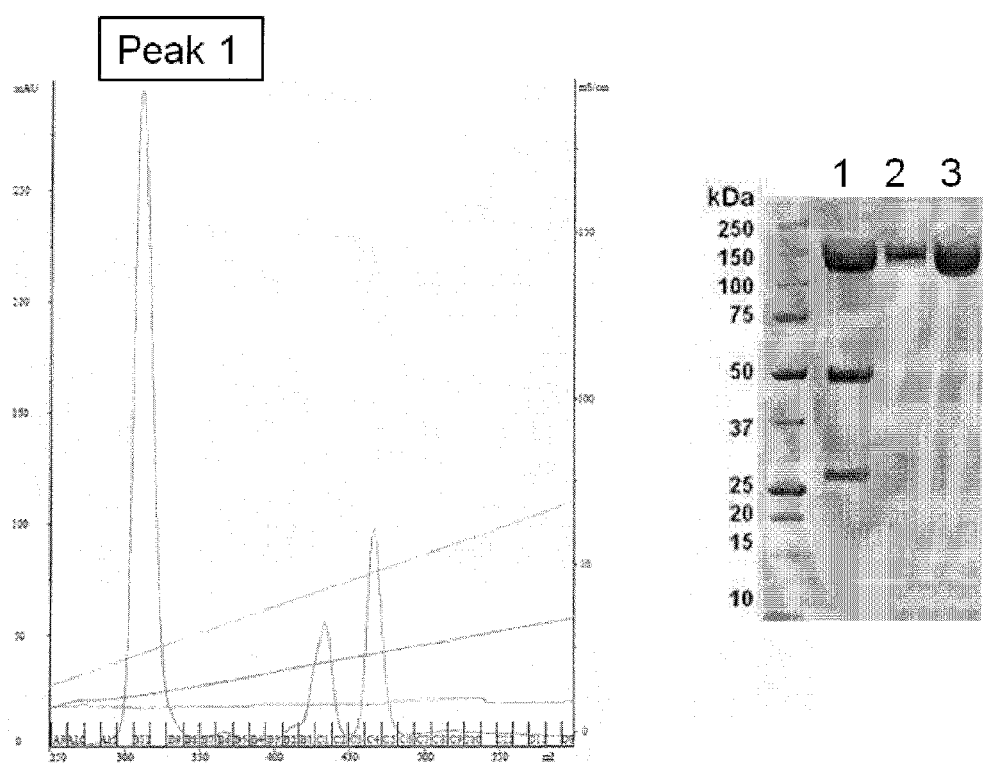

FIG. 12: SP sepharose HP-chromatograpghy (left) and SDS-PAGE (right) under unreduced conditions after pegylation of C96A-Fabs from humanised CD28.3 antibody. Lane 1: MW markers; lane 2: Pegylated proteins pre-chromatography; lane 3: peak 1 containing the monopegylated Fab, representing 41% of the starting material.

Figure 13:
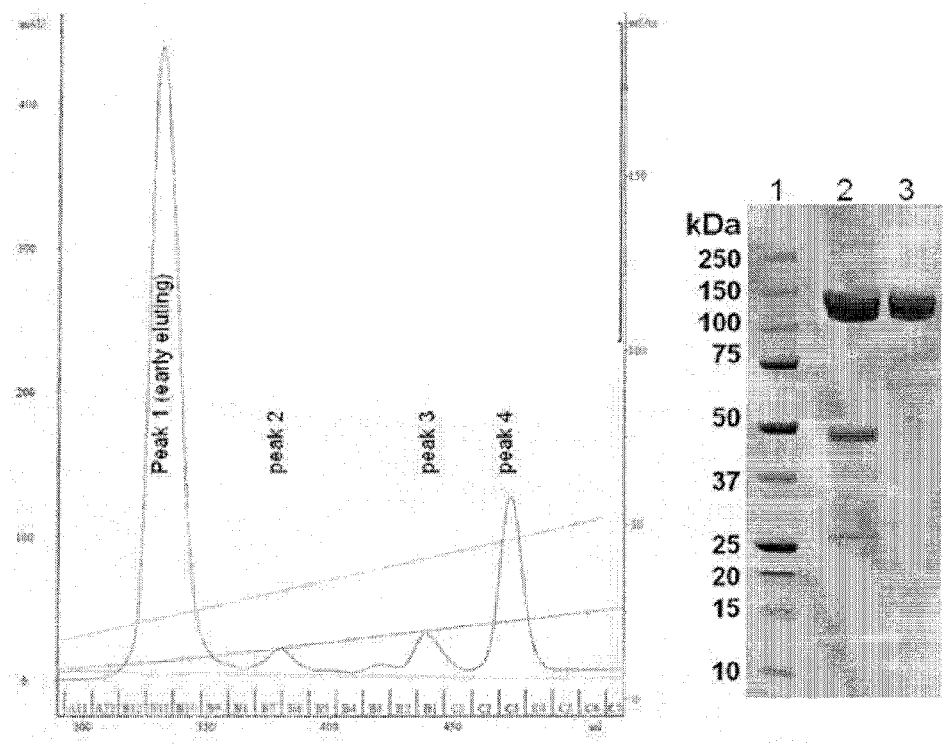

FIG. 13: SP sepharose HP-chromatograpghy (left) and SDS-PAGE (right) under unreduced conditions after pegylation of C96A-Fabs from humanised CD28.3 antibody with a CAA C-terminal sequence in the heavy chain. Lane 1: MW markers; lane 2: Pegylated proteins pre-chromatography; lane 3: peak.

EXAMPLE 1

Construction and Eucaryotic Expression of a hCD28.3 Monovalent Antibody (Fab Fragment)

Heavy Chain:

The sequence encoding the VH region of hCD28.3 (SEQ ID NO: 1) in fusion with the sequence encoding the human CH1 region (NCBI Accession number AAF03881) and with a sequence encoding the leader peptide of the heavy chain of the native murine CD28.3 antibody, was synthetized chemically, and introduced in the cloning vector pGA18 (Geneart) for amplification. The sequence was then excised by digestion with KpnI/BamHI restriction enzymes and subcloned into the KpnI/BamHI sites of the plasmid pcDNA3.1-hygro (Invitrogen). Positive clones were amplified and purified by Midiprep-endotoxin free (Macherey-Nagel) for transfection step.

The resulting plasmid is designated pSignal-VH-hCH1. It comprises a construct containing the sequence encoding the VH region of hCD28.3 between the sequence encoding the CD28.3 heavy chain leader peptide and the sequence encoding the human CH1 region (NCBI Accession number AAF03881). The nucleotidic and amino acid sequences of this construct are shown on FIG. 1. They are also represented as SEQ ID NO: 3 and SEQ ID NO: 4 in the enclosed sequence listing.

Light Chain:

The sequence encoding the VL region of hCD28.3 (SEQ ID NO: 2) in fusion with the sequence encoding the human c kappa region (NCBI accession number BAC01725) and with a sequence encoding the leader peptide of the light chain of the native murine CD28.3 antibody, was synthetized chemically, and introduced in the cloning vector pGA18 (Geneart) for amplification. The sequence was then excised by digestion with KpnI/BamHI restriction enzymes and subcloned into the KpnI/BamHI sites of the plasmid pcDNA3.A-hygro (Invitrogen). Positive clones were amplified and purified by Midiprep-endotoxin free (Macherey-Nagel) for transfection step.

The resulting plasmid is designated pSignal-VL-hCκ. It comprises a construct containing the sequence encoding the VL region of hCD28.3 between the sequence encoding the CD28.3 light chain signal peptide and the sequence encoding the human c kappa region (NCBI accession number BAC01725). The nucleotidic and amino acid sequences of this construct are shown on FIG. 2. They are also represented as SEQ ID NO: 5 and SEQ ID NO: 6 in the enclosed sequence listing.

Eucaryotic Expression

COS cells were co-transfected with 2 μg (each) pSignal-VL-hCH1 and pSignal-VH-hCH1 using the Fugene lipofection kit (Roche Diagnostics, Basel, Switzerland) according to the manufacturer's instructions. Cultures were maintained for 3 days at 37° C., divided one third, and put back into culture for an additional 3 days, after which time the cell supernatants were collected.

The activity of the hCD28.3 monovalent antibody is evaluated directly in the supernatant by ELISA, as described in Example 2 below.

EXAMPLE 2

Detection of the hCD28.3 Fab Fragment Binding Activity by ELISA

The binding properties of the hCD28.3 Fab fragment have been compared with those obtained after transfection of Cos cells with plasmids coding for CD28.3 Fab (not humanized), using two ELISA assays First (Sandwich ELISA), the concentrations of the hCD28.3 and CD28.3 Fab fragments in the culture supernatants of transfected COS cells have been determined using a sandwich ELISA. Briefly, the anti-CD28 Fab contained in the supernatants are first captured by a rabbit polyclonal antibody, specific for the heavy and light variable domains of CD28.3 (obtained after immunization of rabbits with a single-chain-Fv containing the heavy and light variable domains of the native CD28.3, and purified by immunoadsorption on CD28.3 Fab-Sepharose). The captured proteins are then revealed with a murine monoclonal antibody directed to the kappa chain of human IgG, followed by a polyclonal goat anti-mouse antibody labelled with peroxidase. Bound antibody was revealed by colorimetry using the TMB substrate, and read at 405 nm.

The OD corresponding to different dilutions of the supernatant are then compared to a standard curve obtained with known quantities of a CD28.3 Fab, called FR104, purified from culture supernatant of transformed CHO cells with standard techniques of chromatography, and dosed with a BCA (bisynchronic acid) assay. FR104 contains the native (not humanized), VH and VL regions of the CD28.3 antibody. Therefore, we can evaluate the amount of Fab proteins present in cell supernatants.

Second (Binding ELISA), for testing the binding activity of hCD28.3 Fab fragments compared to CD28.3 Fab, chimeric human CD28/Fc (R&D Systems, Abingdon, United Kingdom) was used at 2 µg/ml in carbonate buffer 0.05M pH 9.2 to coat the wells (50 µL/well) of microtiter plates (Nunc Immunoplates) overnight at 4° C. These immobilized CD28 target molecules will bind only immunoreactive molecules with anti-CD28 activity.

The wells were then washed 3 times successively with 200 µL PBS-0.05% Tween, and saturated with 100 µL PBS Tween 0.1% BSA 1% for 2 hours at 37° C.

Then, after 3 washings with 200 µL PBS-0.05% Tween, supernatants containing known concentrations of CD28.3 or hCD28.3 Fab fragments were added (50 µL/well) at different dilutions in PBS-0.1% Tween and incubated for 2 hours at 37° C. After 3 washings with 200 µL PBS-0.05% Tween, a murine monoclonal antibody directed to the kappa chain of human IgG, (1/10000 dilution) was added (1 hour, 37° C.), followed by peroxidase-conjugated goat anti-mouse antibodies (1/2000 dilution), followed by colorimetric revelation using the TMB substrate and reading at 405 nm.

Then the results are plotted as the absorbance (Y axis), measured with the binding ELISA, according to the Fab concentration (X axis), measured with the sandwich ELISA. An AC50 (Antibody Concentration 50) is determined after calculating the slope of the curve in its linear range as the concentration of the anti-CD28 Fab needed to reach 50% of the maximal optical density (OD) in the binding assay.

The results are shown on FIG. 3 and Table I.

FIG. 3A shows the optical density at 405 nm for increasing concentrations of FR104, hCD28.3 Fab or CD28.3 Fab in the Binding ELISA.

FIG. 3 B shows the calculation of the regression curves, allowing for determining comparative AC50 values.

Table I below summarises the OD50, the equation, and the AC50 for the standard FR104, and the Fab fragments VH-wild type+VL-wild type and Fab hCD28.3

TABLE I

|  | OD50 | Equation | AC50 |
|---|---|---|---|
| Std FR104 | 1.792 | y = 1.1424Ln(x) − 3.6351 | 115 |
| CD28.3 Fab | 1.82 | y = 0.9776Ln(x) − 3.2483 | 162 |
| hCD28.3 Fab | 1.804 | y = 1.0217Ln(x) − 3.2859 | 151 |

These results show that 50% of the binding activity to CD28 could be reached at a concentration similar for Fab fragments VH-wild type+VL-wild type (CD28.3 Fab) and hCD28.3 Fab. The concentration is slightly lower for the standard, probably because it is purified before the assay. Thus hCD28.3 retains the CD28-binding properties of the wild type VH and VL sequences of CD28.

EXAMPLE 3

Construction and Eucaryotic Expression of a hCD28.3 Monovalent Antibody (FV-FC Fragment) With a Short γ1 Hinge and a γ4 CH2-CH3 Domain Heavy Chain:

The sequence encoding the VH region of hCD28.3 (SEQ ID NO: 1) in C-terminal fusion with the sequence encoding a portion of the hinge region of the human IgG1 (SEQ ID NO: 8), with CH2-CH3 domains of the human IgG4 (nucleotides 787 to 1440 of the sequence NCBI Accession number BC025985) and in N-terminal position with a sequence encoding the leader peptide of the heavy chain of the native murine CD28.3 antibody, was synthetized chemically, and introduced in the cloning vector pMA (Geneart) for amplification. The sequence was then excised by digestion with NheI/EcoRI restriction enzymes and subcloned into the NheI/EcoRI sites of the plasmid pCIneo (Promega). After transformation of E. coli cells, positive clones were amplified and extracted plasmids were purified by Midiprep-endotoxin free columns (Macherey-Nagel).

The resulting plasmid is designated pSignal-hVH-short-hingeγ1-hγ4CH2-CH3. It comprises a construct containing the sequence encoding the VH region of hCD28.3 between the sequence encoding the CD28.3 heavy chain signal peptide and the sequence encoding a part of the human γ1 hinge region and of the human γ4 CH2-CH3 domains. The nucleotidic and amino acid sequences of this construct are shown on FIG. 4. They are also represented as SEQ ID NO: 9 and SEQ ID NO: 10 in the enclosed sequence listing.

Light Chain:

The sequence encoding the VL region of hCD28.3 (SEQ ID NO: 2) in fusion with the sequence encoding a portion of the hinge region of the human IgG1 (SEQ ID NO: 8), with CH2-CH3 domains of the human IgG4 (nucleotides 787 to 1440 of the sequence NCBI Accession number BC025985) and in N-terminal position with a sequence encoding the leader peptide of the heavy chain of the native murine CD28.3 antibody, was synthetized chemically, and introduced in the cloning vector pMA (Geneart) for amplification. The sequence was then excised by digestion with NheI/EcoRI restriction enzymes and subcloned into the NheI/EcoRI sites of the plasmid pCINeo (Promega). After transformation of E.

*coli* cells, positive clones were amplified and extracted plasmids were purified by Midiprep-endotoxin free columns (Macherey-Nagel).

The resulting plasmid is designated pSignal-hVL-shorthingeγ1-hγ4CH2-CH3. It comprises a construct containing the sequence encoding the VL region of hCD28.3 between the sequence encoding the CD28.3 light chain signal peptide and the sequence encoding a part of the human γ1 hinge region and of the human γ4 CH2-CH3 domains. The nucleotidic and amino acid sequences of this construct are shown on FIG. 5. They are also represented as SEQ ID NO: 11 and SEQ ID NO: 12 in the enclosed sequence listing.

Eukaryotic Expression

COS cells were co-transfected with 1 μg (each) pSignal-hVL-shorthingeγ1-hγ4CH2-CH3 and pSignal-hVH-shorthingeγ1-hγ4CH2-CH3, using the Lipofectamine lipofection kit (Invitrogen) according to the manufacturer's instructions. Cultures were maintained for 3 days at 37° C., after which time the cell supernatants were collected. The activity of the monovalent antibody is evaluated directly in the supernatant by ELISA, as described in Example 5 below.

EXAMPLE 4

Construction and Eucaryotic Expression of a hCD28.3 Monovalent Antibody (FV-FC FRAGMENT) With a Full Length γ1 Hinge and a γ4 CH2-CH3 Domain Heavy Chain:

The sequence encoding the VH region of hCD28.3 (SEQ ID NO: 1) in C-terminal fusion with the sequence encoding a full length hinge region of the human IgG1 (SEQ ID NO: 7), with CH2-CH3 domains of the human IgG4 (nucleotides 787 to 1440 of the sequence NCBI Accession number BC025985) and in N-terminal position with a sequence encoding the leader peptide of the heavy chain of the native murine CD28.3 antibody, was synthetized chemically, and introduced in the cloning vector pMA (Geneart) for amplification. The sequence was then excised by digestion with NheI/EcoRI restriction enzymes and subcloned into the NheI/EcoRI sites of the plasmid pCIneo (Promega). After transformation of *E. coli* cells, positive clones were amplified and extracted plasmids were purified by Midiprep-endotoxin free columns (Macherey-Nagel).

The resulting plasmid is designated pSignal-hVH-fullhingeγ1-hγ4CH2-CH3. It comprises a construct containing the sequence encoding the VH region of hCD28.3 between the sequence encoding the CD28.3 heavy chain signal peptide and the sequence encoding the human γ1 hinge region and the human γ4 CH2-CH3 domains. The nucleotidic and amino acid sequences of this construct are shown on FIG. 6. They are also represented as SEQ ID NO: 13 and SEQ ID NO: 14 in the enclosed sequence listing.

Light Chain:

The sequence encoding the VL region of hCD28.3 (SEQ ID NO: 2) in fusion with the sequence encoding the full length hinge region of the human IgG1 (SEQ ID NO: 7), with CH2-CH3 domains of the human IgG4 (nucleotides 787 to 1440 of the sequence NCBI Accession number BC025985) and in N-terminal position with a sequence encoding the leader peptide of the heavy chain of the native murine CD28.3 antibody, was synthetized chemically, and introduced in the cloning vector pMA (Geneart) for amplification. The sequence was then excised by digestion with NheI/EcoRI restriction enzymes and subcloned into the NheI/EcoRI sites of the plasmid pCIneo (Promega). After transformation of *E. coli* cells, positive clones were amplified and extracted plasmids were purified by Midiprep-endotoxin free columns (Macherey-Nagel).

The resulting plasmid is designated pSignal-hVL-fullhingeγ1-hγ4CH2-CH3. It comprises a construct containing the sequence encoding the VL region of hCD28.3 between the sequence encoding the CD28.3 light chain signal peptide and the sequence encoding the human γ1 full length hinge region and of the human γ4 CH2-CH3 domains. The nucleotidic and amino acid sequences of this construct are shown on FIG. 7. They are also represented as SEQ ID NO: 15 and SEQ ID NO: 16 in the enclosed sequence listing.

Eukaryotic Expression

COS cells were co-transfected with 1 μg (each) pSignal-hVH-fullhingeγ1-hγ4CH2-CH3 and pSignal-hVL-fullhingeγ1-hγ4CH2-CH3 plasmids using the Lipofectamine lipofection kit (Invitrogen) according to the manufacturer's instructions. Cultures were maintained for 3 days at 37° C., after which time the cell supernatants were collected.

The activity of the hCD28.3 monovalent antibody is evaluated directly in the supernatant by ELISA, as described in Example 5 below.

EXAMPLE 5

Evaluation of the HCD28.3-Full Length γ1 Hinge-γ4CH2-CH3 Domains and HCD28.3-Short γ1 Hinge-γ4CH2-CH3 Domains Monovalent Antibodies Binding Activity by ELISA The binding properties of the hCD28.3 monovalent antibodies hCD28.3-full γ1 hinge-γ4CH2-CH3 domains and hCD28.3-short γ1 hinge-γ4CH2-CH3 domains produced by transfected COS cells have been analysed using two ELISA assays.

First (Sandwich ELISA), the concentrations of the hCD28.3 monovalent antibodies in the culture supernatants of transfected COS cells have been determined using a sandwich ELISA. Briefly, the monovalent antibodies contained in the supernatants are first captured by a goat polyclonal antibody directed to human IgG. The captured proteins are then revealed with a biotinylated goat polyclonal anti-human IgG, Fc specific, antibody, then, a Peroxidase-conjugated streptavidin. Bound antibody was revealed by colorimetry using the TMB substrate, and read at 405 nm.

The OD corresponding to different dilutions of the supernatant are then compared to a standard curve obtained with known quantities of hCD28.3 monovalent antibodies, purified from culture supernatant of transformed CHO cells with standard techniques of chromatography, and dosed with a BCA (bisynchronic acid) assay.

Second (Binding ELISA), for testing the binding activity of hCD28.3 monovalent antibodies, chimeric human CD28/Fc (R&D Systems, Abingdon, United Kingdom) was used at 2 μg/ml in carbonate buffer 0.05M pH 9.2 to coat the wells (50 μL/well) of microtiter plates (Nunc Immunoplates) overnight at 4° C. These immobilized CD28 target molecules will bind only immunoreactive molecules with anti-CD28 activity.

The wells were then washed 3 times successively with 200 μL PBS-0.05% Tween, and saturated with 100 μL PBS Tween 0.1% BSA 1% for 2 hours at 37° C.

Then, after 3 washings with 200 μL PBS-0.05% Tween, supernatants containing known concentrations of the monovalent antibodies to be tested were added (50 μL/well) at different dilutions in PBS-0.1% Tween and incubated for 2 hours at 37° C. After 3 washings with 200 µL PBS-0.05% Tween, we added (1/500 dilution; 1 hour, 37° C.) a rabbit polyclonal antiserum, specific for the heavy and light variable domains of CD28.3 (obtained after immunization of rabbits with a single-chain-Fv containing the heavy and light variable domains of the native CD28.3, and purified by immunoadsorption on CD28.3 Fab-Sepharose). This was followed by peroxidase-conjugated donkey anti-rabbit antibodies (1/2000 dilution), followed by colorimetric revelation using the TMB substrate and reading at 405 nm.

Then the results are plotted as the absorbance (Y axis), measured with the binding ELISA, according to the monovalent antibody concentration (X axis), measured with the sandwich ELISA. An AC50 (Antibody Concentration 50) is determined after calculating the slope of the curve in its linear range as the concentration of the monoclonal antibody needed to reach 50% of the maximal optical density (OD) in the binding assay.

FIG. 8 compares binding activities of hCD28.3-full IgG1 hinge-IgG4CH2-CH3 domains with hCD28.3-short IgG1 hinge-IgG4CH2-CH3 domains monovalent antibodies in the Binding ELISA (FIG. 8A).

FIG. 8B summarises the equation, the regression factor and the AC50 for the monovalent antibodies.

These results show that 50% of the binding activity to CD28 could be reached at a concentration similar for hCD28.3-full γ1 hinge-γ4CH2-CH3 domains or hCD28.3-short γ1 hinge-γ4CH2-CH3 domains monovalent antibodies.

EXAMPLE 6 hCD28.3 Monovalent Antibodies Prevents T Cell Activation

To verify that hCD28.3 monovalent antibody blocks CD28-dependent T cell activation, we stimulated human T cells (Jurkat cells) with SEE superantigen presented by a Raji B cell line. The endotoxin SEE, when presented to the class II-positive B cell lymphoblastoid line Raji, activates the Vβ8-expressing T cell line Jurkat to secrete IL-2 (Herman et al, 1990, J. Exp. Med. 172:709). Since Jurkat cells express high level of CD28 and Raji cells express CD80/86, this reaction is partially dependant on CD28. We measured synthesis of interleukin-2 in this assay by ELISA (ELISA Max™ Set Deluxe Human IL-2 Kit; Biolegend #431805) after 48 h, in the presence of increasing concentrations of hVH/VL CD28.3-short γ1 hinge-γ4CH2-CH3 domains.

The results are shown on FIG. 9. They reveal that hCD28.3 monovalent antibodies reduce IL-2 synthesis by T cells in a dose-dependent manner.

EXAMPLE 7

Preparation of a Pegylated hCD28.3 Monovalent Antibody

A hCD28.3 Fab fragment prepared as described in Example 1 was pegylated with maleimide-activated 40 KDa PEG using standard conditions for reduction and PEGylation.

Briefly, Fab antibody fragments were concentrated to 1 mg/mL and then diafiltrated against 20 mM Sodium phosphate, 2 mM EDTA, and pH 7.0. Fab' antibody fragments were then reduced by addition of cysteamine chloride in a molar equivalent ratio=30:1 at room temperature. After 5 hours, solution was applied on a desalting column. Polyethylene glycol (PEG) (Sunbright GL2 400MA, NOF Corporation) was dissolved in 20 mM Phosphate, 2 mM EDTA, pH 7.0 to give 9% (w/w) solution. Desalted Fab solution and PEG were mixed in a molar equivalent ratio=1:1.5 and incubated at ambient temperature for 3 h. Following PEGylation the Fab-peg was purified by chromatography using SP Sepharose HP medium. The target protein was eluted with a salt gradient from 0 to 1 M NaCl. Eluted peaks were analysed by SDS-Page. Peak 1 represented monopegylated material, peak 2 unpegylated material and peak 3 polypegylated material.

The results are shown on FIG. 10.

These results show that a significant part of the Fab proteins from the CD28.3 mAb presents a perturbed pegylation profile which results in a yield of monopegylated Fabs of about 5% only (peak 1).

The CD28.3 mAb contains a cystein residue (C96) that is not engaged in intra or inter-chain dissulfide bridges, at position 96 of the variable domain light chain. Free cystein will possess a higher reactivity than cystein residues engaged into disulfide bridges and will therefore preferentially be targets of maleimide-activated pegs. Therefore it is likely that a second, unwanted pegylation occurs on this residue.

To solve that problem we performed a VL-C96 mutation study to determine whether it was possible to substitute the C96 residue by another amino acid without modifying the binding properties of the antibody.

Plasmid coding for humanized anti-CD28.3 Fabs with unmodified C96 in the light chain, or with C96 to A, G, S, V, T, N or R mutations were constructed and transfected into Cos cells by lipofection, as disclosed in Example 1. Cell supernatants were first analyzed by sandwich ELISA to determine total Fab concentration, as disclosed in Example 2. Then supernatants were analysed by ELISA to determine binding activity on immobilized recombinant CD28, as disclosed in Example 2.

The results are shown in FIG. 11. These results show that unlike all other substitutions tested, the C96A substitution resulted in a fully active antibody and that the C96N substitution resulted only in a moderate reduction of activity.

The C96A Fab fragment variant was pegylated and purified by chromatography as described above. Pegylated proteins pre-chromatography and elution peaks were analysed by SDS-Page. The results are shown on FIG. 12. Peak 1 represents monopegylated material.

These results show that the C96A Fab fragment can be pegylated with an efficacy reaching 41% (FIG. 12).

Advantage of the CAA C-Terminal End of the Heavy Chain.

The immediate molecular environment of a free cystein might modify its accessibility to maleimide-pegylation and therefore modify the yield of the pegylation reaction. One possible option for the C-terminal cystein is to be the last amino acid of the heavy chain. Another option is the addition of "stuff amino acids" at the C-terminal position, after the last cysteine. We therefore compared pegylation efficacy of a Fab' molecule from the C96A variant of the humanized CD28.3 Mab with the last C-terminal cystein being the last amino acid of the heavy chain (C variant; data shown in FIG. 12) with a similar molecule with the last C-terminal cystein being followed by two alanins (CAA variant). Our data clearly and reproducibly demonstrated that the CAA variant could be pegylated with a 20% higher efficacy (FIG. 13). Indeed pegylation yield that was of 41% for the C96A-C variant reached 52% for the C96A-CAA variant.

The invention claimed is:

1. An anti-CD28 antibody selected from the group consisting of:
   (a) an antibody having a CD28-binding site consisting of:
       a heavy chain variable domain of SEQ ID NO: 1; and
       a light chain variable domain of SEQ ID NO: 2, and
   (b) an antibody having a CD28-binding site consisting of:
       a heavy chain variable domain having all three complementarity determining regions (CDRs) of the variable domain of SEQ ID NO: 1; and
       a light chain variable domain having all three CDRs of the variable domain of SEQ ID NO: 2.

2. The antibody of claim 1, which is a monovalent antibody.

3. The monovalent antibody of claim 2, which is a heterodimer of:
   a first protein chain having the sequence of amino-acids 21-251 of SEQ ID NO: 4; and
   a second protein chain having the sequence of amino-acids 21-234 of SEQ ID NO: 6.

4. The monovalent antibody of claim 2, which is a heterodimer of:
   (I) a first protein chain consisting essentially of, from its N-terminus to its C-terminus:
       i: a region A which is a heavy chain variable domain of SEQ ID NO: 1; and
       ii: a region B consisting of a peptide linker followed by the CH2 and CH3 domains of an IgG immunoglobulin, and
   (II) a second protein chain consisting essentially of, from its N-terminus to its C-terminus:
       i: a region A' which is a light chain variable domain of SEQ ID NO: 2; and
       ii: a region B identical to the region B of the first protein chain.

5. The monovalent antibody of claim 4, wherein the peptide linker is selected from the group consisting of:

a peptide of SEQ ID NO: 7; and a peptide of SEQ ID NO: 8.

6. The monovalent antibody of claim 4, wherein the CH2 and CH3 domains are those of an immunoglobulin of the IgG4 subclass.

7. The monovalent antibody according to claim 6, which is selected from the group consisting of:

a monovalent antibody wherein the polypeptide sequence of the first protein chain is the sequence of amino-acids 21-368 of SEQ ID NO: 10, and the polypeptide sequence of the second protein chain is the sequence of amino-acids 21-355 of SEQ ID NO: 12; and a monovalent antibody wherein the polypeptide sequence of the first protein chain is the sequence of amino-acids 21-373 of SEQ ID NO: 14, and the polypeptide sequence of the second protein chain is the sequence of amino-acids 21-360 of SEQ ID NO: 16.

8. The monovalent antibody of claim 3 wherein the second protein chain comprises a variable domain of SEQ ID NO: 2.

9. A polynucleotide selected from the group consisting of:
(a) a polynucleotide encoding a polypeptide having all the CDRs of SEQ ID NO: 1;
(b) a polynucleotide encoding a polypeptide having all the CDRs of SEQ ID NO: 2; and
(c) a polynucleotide encoding an antibody of claim 1.

10. A composition comprising the antibody of claim 2 and a pharmaceutically acceptable excipient.

11. A method of treating a pathological condition selected from the group consisting of transplant rejection, chronic allograft vasculopathy, and graft-versus-host disease in a subject in need thereof comprising administering the anti-CD28 monvalent antibody of claim 2 to the subject.

12. The monovalent antibody of claim 3 wherein the second protein chain comprises a variable domain of SEQ ID NO: 2 where X represents an alanine or an asparagine residue.

13. The monovalent antibody of claim 12 which is pegylated.

14. The antibody of claim 1, wherein the heavy chain variable domain further comprises a Q residue at the N-terminal end.

* * * * *

SEQUENCE LISTING

<160> NUMBER OF SEQ ID NOS: 31

<210> SEQ ID NO 1
<211> LENGTH: 120
<212> TYPE: PRT
<213> ORGANISM: Artificial Sequence
<220> FEATURE:
<223> OTHER INFORMATION: hCD28.3 VH

<400> SEQUENCE: 1

Val Gln Leu Gln Gln Ser Gly Ala Glu Leu Lys Lys Pro Gly Ala Ser
1               5                   10                  15

Val Lys Val Ser Cys Lys Ala Ser Gly Tyr Thr Phe Thr Glu Tyr Ile
            20                  25                  30

Ile His Trp Ile Lys Leu Arg Ser Gly Gln Gly Leu Glu Trp Ile Gly
        35                  40                  45

Trp Phe Tyr Pro Gly Ser Asn Asp Ile Gln Tyr Asn Ala Gln Phe Lys
    50                  55                  60

Gly Lys Ala Thr Leu Thr Ala Asp Lys Ser Ser Ser Thr Val Tyr Met
65                  70                  75                  80

Glu Leu Thr Gly Leu Thr Pro Glu Asp Ser Ala Val Tyr Phe Cys Ala
                85                  90                  95

Arg Arg Asp Asp Phe Ser Gly Tyr Asp Ala Leu Pro Tyr Trp Gly Gln
            100                 105                 110

Gly Thr Leu Val Thr Val Ser Ala
        115                 120

<210> SEQ ID NO 2
<211> LENGTH: 108
<212> TYPE: PRT
<213> ORGANISM: Artificial Sequence
<220> FEATURE:
<223> OTHER INFORMATION: hCD28.3 VL
<220> FEATURE:
<221> NAME/KEY: MISC_FEATURE
<222> LOCATION: (96)..(96)
<223> OTHER INFORMATION: Xaa = Cys, Ala, or Asn

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Lys Thr Asn Glu Asn Ile Tyr Ser Asn
            20                  25                  30

Leu Ala Trp Tyr Gln Gln Lys Asp Gly Lys Ser Pro Gln Leu Leu Ile
        35                  40                  45

Tyr Ala Ala Thr His Leu Val Glu Gly Val Pro Ser Arg Phe Ser Gly
    50                  55                  60

Ser Gly Ser Gly Thr Gln Tyr Ser Leu Thr Ile Ser Ser Leu Gln Pro
65                  70                  75                  80

Glu Asp Phe Gly Asn Tyr Tyr Cys Gln His Phe Trp Gly Thr Pro Xaa
                85                  90                  95

Thr Phe Gly Gly Gly Thr Lys Leu Glu Ile Lys Arg
            100                 105

<210> SEQ ID NO 3
<211> LENGTH: 756
<212> TYPE: DNA
<213> ORGANISM: Artificial Sequence
<220> FEATURE:
<223> OTHER INFORMATION: Signal-VH-hCH1

<400> SEQUENCE: 3

```
atggaatggt gctgggtctt tctcttcctc ctgtcagtaa ctgcaggtgt ccactccaag     60
gtccaactgc agcagtctgg agctgagctg aagaaacccg gggcgtcggt gaaagtctcc    120
tgcaaggcgt ctggttacac cttcactgaa tatattatac actggataaa gctgaggtct    180
ggacagggtc ttgagtggat tgggtggttt taccctggaa gtaatgatat acagtacaat    240
gcgcaattca agggcaaggc acattgact gcggacaaat cctccagcac cgtctatatg     300
gaacttactg gattgacacc cgaggactct gcggtctatt tttgtgcaag acgcgacgat    360
ttctctggtt acgacgccct tccttactgg ggccaaggga ctctggtcac tgtctctgca    420
gctagcacca agggcccatc ggtcttcccc ctggcaccct cctccaagag cacctctggg    480
ggcacagcgg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgacc gtgccctcca gcagcttggg cacccagacc    660
tacatctgca acgtgaatca caagcccagc aacaccaagg tggacaagaa agttgagccc    720
aaatcttgtg acaaaactca cacatgcgcc gcataa                              756
```

<210> SEQ ID NO 4
<211> LENGTH: 251
<212> TYPE: PRT
<213> ORGANISM: Artificial Sequence
<220> FEATURE:
<223> OTHER INFORMATION: Signal-VH-hCH1

<400> SEQUENCE: 4

```
Met Glu Trp Cys Trp Val Phe Leu Phe Leu Leu Ser Val Thr Ala Gly
1               5                   10                  15

Val His Ser Lys Val Gln Leu Gln Gln Ser Gly Ala Glu Leu Lys Lys
            20                  25                  30

Pro Gly Ala Ser Val Lys Val Ser Cys Lys Ala Ser Gly Tyr Thr Phe
        35                  40                  45

Thr Glu Tyr Ile Ile His Trp Ile Lys Leu Arg Ser Gly Gln Gly Leu
    50                  55                  60

Glu Trp Ile Gly Trp Phe Tyr Pro Gly Ser Asn Asp Ile Gln Tyr Asn
65                  70                  75                  80

Ala Gln Phe Lys Gly Lys Ala Thr Leu Thr Ala Asp Lys Ser Ser Ser
                85                  90                  95

Thr Val Tyr Met Glu Leu Thr Gly Leu Thr Pro Glu Asp Ser Ala Val
            100                 105                 110

Tyr Phe Cys Ala Arg Arg Asp Asp Phe Ser Gly Tyr Asp Ala Leu Pro
        115                 120                 125

Tyr Trp Gly Gln Gly Thr Leu Val Thr Val Ser Ala Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220
```

Val Asn His Lys Pro Ser Asn Thr Lys Val Asp Lys Val Glu Pro
225                 230                 235                 240

Lys Ser Cys Asp Lys Thr His Thr Cys Ala Ala
                245                 250

<210> SEQ ID NO 5
<211> LENGTH: 705
<212> TYPE: DNA
<213> ORGANISM: Artificial Sequence
<220> FEATURE:
<223> OTHER INFORMATION: Signal-VL-hCkappa

<400> SEQUENCE: 5

```
atgagtgtgc ccactcaggt cctggggttg ctgctgctgt ggcttacaga tgccagatgt     60
gacatccaga tgactcagtc tccatcttcc ctatctgcat ctgtgggaga cagggtcacc    120
atcacgtgta aaacaaatga gaatatttac agtaatttag catggtatca gcagaaagac    180
ggaaaatctc ctcagctcct gatctatgct gcaacacact tagtagaggg tgtgccatca    240
aggttcagtg gcagtggatc aggcacacag tattccctca caatcagcag cctgcagcca    300
gaagattttg gaattatta ctgtcaacac ttttggggta ctccgtgcac gttcggaggg    360
gggaccaagc tggaaataaa acggacggtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagttcgc ccgtcacaaa gagcttcaac aggggagagt gttaa                    705
```

<210> SEQ ID NO 6
<211> LENGTH: 234
<212> TYPE: PRT
<213> ORGANISM: Artificial Sequence
<220> FEATURE:
<223> OTHER INFORMATION: Signal-VL-hCkappa
<220> FEATURE:
<221> NAME/KEY: MISC_FEATURE
<222> LOCATION: (116)..(116)
<223> OTHER INFORMATION: Xaa = Cys or Ala

<400> SEQUENCE: 6

Met Ser Val Pro Thr Gln Val Leu Gly Leu Leu Leu Trp Leu Thr
1               5                   10                  15

Asp Ala Arg Cys Asp Ile Gln Met Thr Gln Ser Pro Ser Ser Leu Ser
                20                  25                  30

Ala Ser Val Gly Asp Arg Val Thr Ile Thr Cys Lys Thr Asn Glu Asn
            35                  40                  45

Ile Tyr Ser Asn Leu Ala Trp Tyr Gln Gln Lys Asp Gly Lys Ser Pro
    50                  55                  60

Gln Leu Leu Ile Tyr Ala Ala Thr His Leu Val Glu Gly Val Pro Ser
65                  70                  75                  80

Arg Phe Ser Gly Ser Gly Ser Gly Thr Gln Tyr Ser Leu Thr Ile Ser
                85                  90                  95

Ser Leu Gln Pro Glu Asp Phe Gly Asn Tyr Tyr Cys Gln His Phe Trp
            100                 105                 110

Gly Thr Pro Xaa Thr Phe Gly Gly Gly Thr Lys Leu Glu Ile Lys Arg
    115                 120                 125

```
Thr Val Ala Ala Pro Ser Val Phe Ile Phe Pro Ser Asp Glu Gln
    130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                165                 170                 175
Gly Asn Ser Gln Glu Ser Val Thr Glu Gln Asp Ser Lys Asp Ser Thr
            180                 185                 190
Tyr Ser Leu Ser Ser Thr Leu Thr Leu Ser Lys Ala Asp Tyr Glu Lys
        195                 200                 205
His Lys Val Tyr Ala Cys Glu Val Thr His Gln Gly Leu Ser Ser Pro
    210                 215                 220
Val Thr Lys Ser Phe Asn Arg Gly Glu Cys
225                 230
```

<210> SEQ ID NO 7
<211> LENGTH: 15
<212> TYPE: PRT
<213> ORGANISM: Homo sapiens

<400> SEQUENCE: 7

```
Glu Pro Lys Ser Cys Asp Lys Thr His Thr Cys Pro Pro Cys Pro
1               5                   10                  15
```

<210> SEQ ID NO 8
<211> LENGTH: 10
<212> TYPE: PRT
<213> ORGANISM: Homo sapiens

<400> SEQUENCE: 8

```
Asp Lys Thr His Thr Cys Pro Pro Cys Pro
1               5                   10
```

<210> SEQ ID NO 9
<211> LENGTH: 1107
<212> TYPE: DNA
<213> ORGANISM: Artificial Sequence
<220> FEATURE:
<223> OTHER INFORMATION: hVHCD28.3-short hingegamma1-hgamma4CH2CH3

<400> SEQUENCE: 9

```
atggaatggt gctgggtgtt cctgttcctg ctgtccgtga ccgctggcgt gcactccaag    60
caggtgcagc tgcagcagtc tggcgccgag ctgaagaagc ctggcgcctc cgtcaaggtg   120
tcctgcaagg cctccggcta caccttcacc gagtacatca tccactggat caagctgaga   180
tccggccagg gctggaatg gatcggctgg ttctaccctg ctccaacga catccagtac   240
aacgccagt tcaagggcaa ggccaccctg accgccgaca gtcctcctc caccgtgtac   300
atggaactga ccggcctgac ccctgaggac tccgccgtgt acttctgcgc caggcgggac   360
gacttctctg gctacgacgc cctgccttat tggggccagg gcaccctggt gaccgtgtcc   420
gccgacaaaa ctcacacatg cccaccgtgc ccagcacctg agttcctggg gggaccatca   480
gtcttcctgt tccccccaaa acccaaggac actctcatga tctcccggac ccctgaggtc   540
acgtgcgtgg tggtggacgt gagccaggaa gaccccgagg tccagttcaa ctggtacgtg   600
gatggcgtgg aggtgcataa tgccaagaca aagccgcggg aggagcagtt caacagcacg   660
taccgtgtgg tcagcgtcct caccgtcctg caccaggact ggctgaacgg caaggagtac   720
aagtgcaagg tctccaacaa aggcctcccg tcctccatcg agaaaaccat ctccaaagcc   780
```

```
aaagggcagc ccgagagcc acaggtgtac accctgcccc catcccagga ggagatgacc    840
aagaaccagg tcagcctgac ctgcctggtc aaaggcttct accccagcga catcgccgtg    900
gagtgggaga gcaatgggca gccggagaac aactacaaga ccacgcctcc cgtgctggac    960
tccgacggct ccttcttcct ctacagcagg ctcaccgtgg acaagagcag gtggcaggag   1020
gggaatgtct tctcatgctc cgtgatgcat gaggctctgc acaaccacta cacacagaag   1080
agcctctccc tgtctctggg taaatga                                       1107
```

<210> SEQ ID NO 10
<211> LENGTH: 368
<212> TYPE: PRT
<213> ORGANISM: Artificial
<220> FEATURE:
<223> OTHER INFORMATION: hVHCD28.3-short hingegamma1-hgamma4CH2CH3

<400> SEQUENCE: 10

```
Met Glu Trp Cys Trp Val Phe Leu Phe Leu Leu Ser Val Thr Ala Gly
1               5                   10                  15

Val His Ser Lys Gln Val Gln Leu Gln Gln Ser Gly Ala Glu Leu Lys
            20                  25                  30

Lys Pro Gly Ala Ser Val Lys Val Ser Cys Lys Ala Ser Gly Tyr Thr
        35                  40                  45

Phe Thr Glu Tyr Ile Ile His Trp Ile Lys Leu Arg Ser Gly Gln Gly
    50                  55                  60

Leu Glu Trp Ile Gly Trp Phe Tyr Pro Gly Ser Asn Asp Ile Gln Tyr
65                  70                  75                  80

Asn Ala Gln Phe Lys Gly Lys Ala Thr Leu Thr Ala Asp Lys Ser Ser
                85                  90                  95

Ser Thr Val Tyr Met Glu Leu Thr Gly Leu Thr Pro Glu Asp Ser Ala
            100                 105                 110

Val Tyr Phe Cys Ala Arg Arg Asp Asp Phe Ser Gly Tyr Asp Ala Leu
        115                 120                 125

Pro Tyr Trp Gly Gln Gly Thr Leu Val Thr Val Ser Ala Asp Lys Thr
    130                 135                 140

His Thr Cys Pro Pro Cys Pro Ala Pro Glu Phe Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser Gln Glu Asp Pro
            180                 185                 190

Glu Val Gln Phe Asn Trp Tyr Val Asp Gly Val Glu Val His Asn Ala
        195                 200                 205

Lys Thr Lys Pro Arg Glu Glu Gln Phe Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Gly Leu Pro Ser Ser Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Gln Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300
```

```
Asn Gly Gln Pro Glu Asn Asn Tyr Lys Thr Thr Pro Pro Val Leu Asp
305                 310                 315                 320

Ser Asp Gly Ser Phe Phe Leu Tyr Ser Arg Leu Thr Val Asp Lys Ser
            325                 330                 335

Arg Trp Gln Glu Gly Asn Val Phe Ser Cys Ser Val Met His Glu Ala
        340                 345                 350

Leu His Asn His Tyr Thr Gln Lys Ser Leu Ser Leu Ser Leu Gly Lys
    355                 360                 365

<210> SEQ ID NO 11
<211> LENGTH: 1068
<212> TYPE: DNA
<213> ORGANISM: Artificial Sequence
<220> FEATURE:
<223> OTHER INFORMATION: hVLCD28.3-short hingegamma1-hgamma4CH2CH3

<400> SEQUENCE: 11
atgtccgtgc ctacccaggt gctgggactg ctgctgctgt ggctgaccga cgccagatgc      60
gacatccaga tgacccagtc ccctcctcc ctgtctgcct ccgtgggcga ccgggtgacc     120
atcacctgta agaccaacga gaacatctac tccaacctgg cctggtatca gcagaaggac     180
ggcaagtccc ctcagctgct gatctacgcc gccacccatc tggtggaggg cgtgccctct     240
agattctccg gctccggctc tggcacccag tactccctga ccatcagctc cctgcagcct     300
gaggacttcg caactactac tgccagcac ttctggggca cccttgtac cttcggcgga     360 ggcaccaagc tggaaatcaa gcgggacaaa actcacacat gcccaccgtg cccagcacct     420
gagttcctgg ggggaccatc agtcttcctg ttccccccaa aacccaagga cactctcatg     480
atctcccgga cccctgaggt cacgtgcgtg gtggtggacg tgagccagga agaccccgag     540
gtccagttca actggtacgt ggatggcgtg gaggtgcata atgccaagac aaagccgcgg     600
gaggagcagt tcaacagcac gtaccgtgtg gtcagcgtcc tcaccgtcct gcaccaggac     660
tggctgaacg gcaaggagta caagtgcaag gtctccaaca aaggcctccc gtcctccatc     720
gagaaaacca tctccaaagc caaagggcag ccccgagagc cacaggtgta caccctgccc     780
ccatcccagg aggagatgac caagaaccag gtcagcctga cctgcctggt caaaggcttc     840
taccccagcg acatcgccgt ggagtgggag agcaatgggc agccggagaa caactacaag     900
accacgcctc ccgtgctgga ctccgacggc tccttcttcc tctacagcag gctcaccgtg     960
gacaagagca ggtggcagga ggggaatgtc ttctcatgct ccgtgatgca tgaggctctg    1020
cacaaccact acacacagaa gagcctctcc ctgtctctgg gtaaatga               1068

<210> SEQ ID NO 12
<211> LENGTH: 355
<212> TYPE: PRT
<213> ORGANISM: Artificial Sequence
<220> FEATURE:
<223> OTHER INFORMATION: hVLCD28.3-short hingegamma1-hgamma4CH2CH3

<400> SEQUENCE: 12

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Lys Thr Asn Glu Asn
        35                  40                  45

Ile Tyr Ser Asn Leu Ala Trp Tyr Gln Gln Lys Asp Gly Lys Ser Pro
    50                  55                  60
```

Gln Leu Leu Ile Tyr Ala Ala Thr His Leu Val Glu Gly Val Pro Ser
65                  70                  75                  80

Arg Phe Ser Gly Ser Gly Ser Gly Thr Gln Tyr Ser Leu Thr Ile Ser
            85                  90                  95

Ser Leu Gln Pro Glu Asp Phe Gly Asn Tyr Tyr Cys Gln His Phe Trp
            100                 105                 110

Gly Thr Pro Cys Thr Phe Gly Gly Gly Thr Lys Leu Glu Ile Lys Arg
            115                 120                 125

Asp Lys Thr His Thr Cys Pro Pro Cys Pro Ala Pro Glu Phe Leu Gly
            130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser Gln
            165                 170                 175

Glu Asp Pro Glu Val Gln Phe Asn Trp Tyr Val Asp Gly Val Glu Val
            180                 185                 190

His Asn Ala Lys Thr Lys Pro Arg Glu Glu Gln Phe Asn Ser Thr Tyr
            195                 200                 205

Arg Val Val Ser Val Leu Thr Val Leu His Gln Asp Trp Leu Asn Gly
210                 215                 220

Lys Glu Tyr Lys Cys Lys Val Ser Asn Lys Gly Leu Pro Ser Ser Ile
225                 230                 235                 240

Glu Lys Thr Ile Ser Lys Ala Lys Gly Gln Pro Arg Glu Pro Gln Val
            245                 250                 255

Tyr Thr Leu Pro Pro Ser Gln Glu Glu Met Thr Lys Asn Gln Val Ser
            260                 265                 270

Leu Thr Cys Leu Val Lys Gly Phe Tyr Pro Ser Asp Ile Ala Val Glu
            275                 280                 285

Trp Glu Ser Asn Gly Gln Pro Glu Asn Asn Tyr Lys Thr Thr Pro Pro
290                 295                 300

Val Leu Asp Ser Asp Gly Ser Phe Phe Leu Tyr Ser Arg Leu Thr Val
305                 310                 315                 320

Asp Lys Ser Arg Trp Gln Glu Gly Asn Val Phe Ser Cys Ser Val Met
            325                 330                 335

His Glu Ala Leu His Asn His Tyr Thr Gln Lys Ser Leu Ser Leu Ser
            340                 345                 350

Leu Gly Lys
        355

<210> SEQ ID NO 13
<211> LENGTH: 1122
<212> TYPE: DNA
<213> ORGANISM: Artificial Sequence
<220> FEATURE:
<223> OTHER INFORMATION: hVHCD28.3-full hingegamma1-hgamma4CH2CH3

<400> SEQUENCE: 13
atggaatggt gctgggtgtt cctgttcctg ctgtccgtga ccgctggcgt gcactccaag      60
caggtgcagc tgcagcagtc tggcgccgag ctgaagaagc ctggcgccct cgtcaaggtg     120
tcctgcaagg cctccggcta caccttcacc gagtacatca tccactggat caagctgaga     180
tccggccagg gcctggaatg gatcggctgg ttctaccctg ctccaacga catccagtac     240 aacgcccagt tcaagggcaa ggccaccctg accgccgaca gtcctcctc caccgtgtac     300 atggaactga ccggcctgac ccctgaggac tccgccgtgt acttctgcgc caggcgggac     360

```
gacttctctg gctacgacgc cctgccttat tggggccagg gcaccctggt gaccgtgtcc    420
gccgagccca atcttgtga caaaactcac acatgcccac cgtgcccagc acctgagttc     480 ctgggggac catcagtctt cctgttcccc ccaaaaccca aggacactct catgatctcc     540
cggacccctg aggtcacgtg cgtggtggtg gacgtgagcc aggaagaccc cgaggtccag    600
ttcaactggt acgtggatgg cgtggaggtg cataatgcca agacaaagcc gcgggaggag    660
cagttcaaca gcacgtaccg tgtggtcagc gtcctcaccg tcctgcacca ggactggctg    720
aacggcaagg agtacaagtg caaggtctcc aacaaaggcc tcccgtcctc catcgagaaa    780
accatctcca aagccaaagg gcagccccga gagccacagg tgtacaccct gcccccatcc    840
caggaggaga tgaccaagaa ccaggtcagc ctgacctgcc tggtcaaagg cttctacccc    900
agcgacatcg ccgtggagtg ggagagcaat gggcagccgg agaacaacta caagaccacg    960
cctcccgtgc tggactccga cggctccttc ttcctctaca gcaggctcac cgtggacaag   1020
agcaggtggc aggaggggaa tgtcttctca tgctccgtga tgcatgaggc tctgcacaac   1080
cactacacac agaagagcct ctccctgtct ctgggtaaat ga                      1122
```

<210> SEQ ID NO 14
<211> LENGTH: 373
<212> TYPE: PRT
<213> ORGANISM: Artificial Sequence
<220> FEATURE:
<223> OTHER INFORMATION: hVHCD28.3-full hingegamma1-hgamma4CH2CH3

<400> SEQUENCE: 14

```
Met Glu Trp Cys Trp Val Phe Leu Phe Leu Leu Ser Val Thr Ala Gly
1               5                   10                  15

Val His Ser Lys Gln Val Gln Leu Gln Gln Ser Gly Ala Glu Leu Lys
            20                  25                  30

Lys Pro Gly Ala Ser Val Lys Val Ser Cys Lys Ala Ser Gly Tyr Thr
        35                  40                  45

Phe Thr Glu Tyr Ile Ile His Trp Ile Lys Leu Arg Ser Gly Gln Gly
    50                  55                  60

Leu Glu Trp Ile Gly Trp Phe Tyr Pro Gly Ser Asn Asp Ile Gln Tyr
65                  70                  75                  80

Asn Ala Gln Phe Lys Gly Lys Ala Thr Leu Thr Ala Asp Lys Ser Ser
                85                  90                  95

Ser Thr Val Tyr Met Glu Leu Thr Gly Leu Thr Pro Glu Asp Ser Ala
            100                 105                 110

Val Tyr Phe Cys Ala Arg Arg Asp Asp Phe Ser Gly Tyr Asp Ala Leu
        115                 120                 125

Pro Tyr Trp Gly Gln Gly Thr Leu Val Thr Val Ser Ala Glu Pro Lys
    130                 135                 140

Ser Cys Asp Lys Thr His Thr Cys Pro Pro Cys Pro Ala Pro Glu Phe
145                 150                 155                 160

Leu Gly Gly Pro Ser Val Phe Leu Phe Pro Pro Lys Pro Lys Asp Thr
                165                 170                 175

Leu Met Ile Ser Arg Thr Pro Glu Val Thr Cys Val Val Val Asp Val
            180                 185                 190

Ser Gln Glu Asp Pro Glu Val Gln Phe Asn Trp Tyr Val Asp Gly Val
        195                 200                 205

Glu Val His Asn Ala Lys Thr Lys Pro Arg Glu Glu Gln Phe Asn Ser
    210                 215                 220
```

```
Thr Tyr Arg Val Val Ser Val Leu Thr Val Leu His Gln Asp Trp Leu
225                 230                 235                 240

Asn Gly Lys Glu Tyr Lys Cys Lys Val Ser Asn Lys Gly Leu Pro Ser
            245                 250                 255

Ser Ile Glu Lys Thr Ile Ser Lys Ala Lys Gly Gln Pro Arg Glu Pro
        260                 265                 270

Gln Val Tyr Thr Leu Pro Pro Ser Gln Glu Glu Met Thr Lys Asn Gln
    275                 280                 285

Val Ser Leu Thr Cys Leu Val Lys Gly Phe Tyr Pro Ser Asp Ile Ala
290                 295                 300

Val Glu Trp Glu Ser Asn Gly Gln Pro Glu Asn Asn Tyr Lys Thr Thr
305                 310                 315                 320

Pro Pro Val Leu Asp Ser Asp Gly Ser Phe Phe Leu Tyr Ser Arg Leu
                325                 330                 335

Thr Val Asp Lys Ser Arg Trp Gln Glu Gly Asn Val Phe Ser Cys Ser
            340                 345                 350

Val Met His Glu Ala Leu His Asn His Tyr Thr Gln Lys Ser Leu Ser
        355                 360                 365

Leu Ser Leu Gly Lys
    370
```

<210> SEQ ID NO 15
<211> LENGTH: 1083
<212> TYPE: DNA
<213> ORGANISM: Artificial Sequence
<220> FEATURE:
<223> OTHER INFORMATION: hVLCD28.3-full hingegamma1-hgamma4CH2CH3

<400> SEQUENCE: 15

```
atgtccgtgc ctacccaggt gctgggactg ctgctgctgt ggctgaccga cgccagatgc        60
gacatccaga tgacccagtc ccctcctcc ctgtctgcct ccgtgggcga ccgggtgacc       120
atcacctgta agaccaacga gaacatctac tccaacctgg cctggtatca gcagaaggac       180
ggcaagtccc ctcagctgct gatctacgcc gccacccatc tggtggaggg cgtgccctct       240
agattctccg gctccggctc tggcacccag tactccctga ccatcagctc cctgcagcct       300
gaggacttcg gcaactacta ctgccagcac ttctgggca cccttgtac cttcggcgga       360 ggcaccaagc tggaaatcaa gcgggagccc aaatcttgtg acaaaactca cacatgccca       420
ccgtgcccag cacctgagtt cctggggggga ccatcagtct tcctgttccc cccaaaaccc       480
aaggacactc tcatgatctc ccggacccct gaggtcacgt gcgtggtggt ggacgtgagc       540
caggaagacc ccgaggtcca gttcaactgg tacgtggatg gcgtggaggt gcataatgcc       600
aagacaaagc cgcgggagga gcagttcaac agcacgtacc gtgtggtcag cgtcctcacc       660
gtcctgcacc aggactggct gaacggcaag gagtacaagt gcaaggtctc caacaaaggc       720
ctcccgtcct ccatcgagaa aaccatctcc aaagccaaag gcagccccg agagccacag       780 gtgtacaccc tgccccatc ccaggaggag atgaccaaga accaggtcag cctgacctgc       840
ctggtcaaag gcttctaccc cagcgacatc gccgtggagt gggagagcaa tgggcagccg       900
gagaacaact acaagaccac gcctcccgtg ctggactccg acggctcctt cttcctctac       960
agcaggctca ccgtggacaa gagcaggtgg caggagggga atgtcttctc atgctccgtg      1020
atgcatgagg ctctgcacaa ccactacaca cagaagagcc tctccctgtc tctgggtaaa      1080
tga                                                                     1083
```

```
<210> SEQ ID NO 16
<211> LENGTH: 360
<212> TYPE: PRT
<213> ORGANISM: Artificial Sequence
<220> FEATURE:
<223> OTHER INFORMATION: hVLCD28.3-full hingegamma1-hgamma4CH2CH3

<400> SEQUENCE: 16

Met Ser Val Pro Thr Gln Val Leu Gly Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Lys Thr Asn Glu Asn
        35                  40                  45

Ile Tyr Ser Asn Leu Ala Trp Tyr Gln Gln Lys Asp Gly Lys Ser Pro
    50                  55                  60

Gln Leu Leu Ile Tyr Ala Ala Thr His Leu Val Glu Gly Val Pro Ser
65                  70                  75                  80

Arg Phe Ser Gly Ser Gly Ser Gly Thr Gln Tyr Ser Leu Thr Ile Ser
                85                  90                  95

Ser Leu Gln Pro Glu Asp Phe Gly Asn Tyr Tyr Cys Gln His Phe Trp
            100                 105                 110

Gly Thr Pro Cys Thr Phe Gly Gly Gly Thr Lys Leu Glu Ile Lys Arg
        115                 120                 125

Glu Pro Lys Ser Cys Asp Lys Thr His Thr Cys Pro Pro Cys Pro Ala
    130                 135                 140

Pro Glu Phe Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser Gln Glu Asp Pro Glu Val Gln Phe Asn Trp Tyr Val
            180                 185                 190

Asp Gly Val Glu Val His Asn Ala Lys Thr Lys Pro Arg Glu Glu Gln
        195                 200                 205

Phe Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Gly
225                 230                 235                 240

Leu Pro Ser Ser Ile Glu Lys Thr Ile Ser Lys Ala Lys Gly Gln Pro
                245                 250                 255

Arg Glu Pro Gln Val Tyr Thr Leu Pro Pro Ser Gln Glu Glu Met Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Arg Leu Thr Val Asp Lys Ser Arg Trp Gln Glu Gly Asn Val Phe
                325                 330                 335

Ser Cys Ser Val Met His Glu Ala Leu His Asn His Tyr Thr Gln Lys
            340                 345                 350

Ser Leu Ser Leu Ser Leu Gly Lys
        355                 360
```

```
<210> SEQ ID NO 17
<211> LENGTH: 60
<212> TYPE: DNA
<213> ORGANISM: Artificial Sequence
<220> FEATURE:
<223> OTHER INFORMATION: Nucleotide for leader sequence

<400> SEQUENCE: 17
atggaatggt gctgggtctt tctcttcctc ctgtcagtaa ctgcaggtgt ccactccaag      60

<210> SEQ ID NO 18
<211> LENGTH: 20
<212> TYPE: PRT
<213> ORGANISM: Artificial Sequence
<220> FEATURE:
<223> OTHER INFORMATION: Amind acid for leader sequence

<400> SEQUENCE: 18

Met Glu Trp Cys Trp Val Phe Leu Phe Leu Leu Ser Val Thr Ala Gly
1               5                   10                  15

Val His Ser Lys
            20

<210> SEQ ID NO 19
<211> LENGTH: 4
<212> TYPE: PRT
<213> ORGANISM: Artificial Sequence
<220> FEATURE:
<223> OTHER INFORMATION: AA - VH - CDR1

<400> SEQUENCE: 19

Thr Glu Tyr Ile
1

<210> SEQ ID NO 20
<211> LENGTH: 17
<212> TYPE: PRT
<213> ORGANISM: Artificial Sequence
<220> FEATURE:
<223> OTHER INFORMATION: AA - VH - CDR2

<400> SEQUENCE: 20

Ile Gly Trp Phe Tyr Pro Gly Ser Asn Asp Ile Gln Tyr Asn Ala Gln
1               5                   10                  15

Phe

<210> SEQ ID NO 21
<211> LENGTH: 13
<212> TYPE: PRT
<213> ORGANISM: Artificial Sequence
<220> FEATURE:
<223> OTHER INFORMATION: AA - VH - CDR3

<400> SEQUENCE: 21

Ala Arg Arg Asp Asp Phe Ser Gly Tyr Asp Ala Leu Pro
1               5                   10

<210> SEQ ID NO 22
<211> LENGTH: 336
<212> TYPE: DNA
<213> ORGANISM: Artificial Sequence
<220> FEATURE:
<223> OTHER INFORMATION: VT - hCH1

<400> SEQUENCE: 22
gctagcacca agggcccatc ggtcttcccc ctggcaccct cctccaagag cacctctggg      60
```

-continued

```
ggcacagcgg ccctgggctg cctggtcaag gactacttcc ccgaaccggt gacggtgtcg      120
tggaactcag gcgccctgac cagcggcgtg cacaccttcc cggctgtcct acagtcctca      180
ggactctact ccctcagcag cgtggtgacc gtgccctcca gcagcttggg cacccagacc      240
tacatctgca acgtgaatca caagcccagc aacaccaagg tggacaagaa agttgagccc      300
aaatcttgtg acaaaactca cacatgcgcc gcataa                                336
```

```
<210> SEQ ID NO 23
<211> LENGTH: 100
<212> TYPE: PRT
<213> ORGANISM: Artificial Sequence
<220> FEATURE:
<223> OTHER INFORMATION: AA - hCH1

<400> SEQUENCE: 23
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro
            100

```
<210> SEQ ID NO 24
<211> LENGTH: 60
<212> TYPE: DNA
<213> ORGANISM: Artificial Sequence
<220> FEATURE:
<223> OTHER INFORMATION: NT - leader seq

<400> SEQUENCE: 24
atgagtgtgc ccactcaggt cctggggttg ctgctgctgt ggcttacaga tgccagatgt      60
```

```
<210> SEQ ID NO 25
<211> LENGTH: 20
<212> TYPE: PRT
<213> ORGANISM: Artificial Sequence
<220> FEATURE:
<223> OTHER INFORMATION: AA - leader seq

<400> SEQUENCE: 25
```

Met Ser Val Pro Thr Gln Val Leu Gly Leu Leu Leu Leu Trp Leu Thr
1               5                   10                  15

Asp Ala Arg Cys
            20

```
<210> SEQ ID NO 26
<211> LENGTH: 8
<212> TYPE: PRT
<213> ORGANISM: Artificial Sequence
<220> FEATURE:
<223> OTHER INFORMATION: aa - vl - CDR1

<400> SEQUENCE: 26
```

Asn Leu Ala Trp Tyr Gln Gln Lys
1               5

<210> SEQ ID NO 27
<211> LENGTH: 8
<212> TYPE: PRT
<213> ORGANISM: Artificial Sequence
<220> FEATURE:
<223> OTHER INFORMATION: aa - vl - CDR2

<400> SEQUENCE: 27

Ala Ala Thr His Leu Val Glu Gly
1               5

<210> SEQ ID NO 28
<211> LENGTH: 7
<212> TYPE: PRT
<213> ORGANISM: Artificial Sequence
<220> FEATURE:
<223> OTHER INFORMATION: aa - vl - CDR3

<400> SEQUENCE: 28

His Phe Trp Gly Thr Pro Cys
1               5

<210> SEQ ID NO 29
<211> LENGTH: 318
<212> TYPE: DNA
<213> ORGANISM: Artificial Sequence
<220> FEATURE:
<223> OTHER INFORMATION: NT - human c kappa region

<400> SEQUENCE: 29
gtggctgcac catctgtctt catcttcccg ccatctgatg agcagttgaa atctggaact      60
gcctctgttg tgtgcctgct gaataacttc tatcccagag aggccaaagt acagtggaag     120
gtggataacg ccctccaatc gggtaactcc caggagagtg tcacagagca ggacagcaag     180
gacagcacct acagcctcag cagcaccctg acgctgagca agcagactac gagaaacac     240 aaagtctacg cctgcgaagt cacccatcag ggcctgagtt cgcccgtcac aaagagcttc     300
aacaggggag agtgttaa                                                  318

<210> SEQ ID NO 30
<211> LENGTH: 105
<212> TYPE: PRT
<213> ORGANISM: Artificial Sequence
<220> FEATURE:
<223> OTHER INFORMATION: aa - human c kappa region

<400> SEQUENCE: 30

Val Ala Ala Pro Ser Val Phe Ile Phe Pro Pro Ser Asp Glu Gln Leu
1               5                   10                  15

Lys Ser Gly Thr Ala Ser Val Val Cys Leu Leu Asn Asn Phe Tyr Pro
            20                  25                  30

Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
    50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Ser Pro Val
                85                  90                  95

```
Thr Lys Ser Phe Asn Arg Gly Glu Cys
            100                 105

<210> SEQ ID NO 31
<211> LENGTH: 217
<212> TYPE: PRT
<213> ORGANISM: Artificial Sequence
<220> FEATURE:
<223> OTHER INFORMATION: CH2-CH3 domains

<400> SEQUENCE: 31

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
            115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
            195                 200                 205

Lys Ser Leu Ser Leu Ser Leu Gly Lys
210                 215
```